United States Patent
Pandey et al.

(10) Patent No.: US 10,179,156 B2
(45) Date of Patent: Jan. 15, 2019

(54) MEDICAMENT CONTAINING TARAXACUM PLANT ROOT EXTRACT FOR TREATMENT OR PREVENTION OF CANCER, AND METHOD FOR PREPARING SAME

(71) Applicants: Siyaram Pandey, Lasalle (CA); Caroline Marie Hamm, Wheatley (CA); Pamela Uzuazo Ovadje, Windsor (CA)

(72) Inventors: Siyaram Pandey, Lasalle (CA); Caroline Marie Hamm, Wheatley (CA); Pamela Uzuazo Ovadje, Windsor (CA)

(*) Notice: Subject to any disclaimer, the term of this patent is extended or adjusted under 35 U.S.C. 154(b) by 430 days.

(21) Appl. No.: 14/377,418

(22) PCT Filed: Feb. 8, 2013

(86) PCT No.: PCT/CA2013/000114
§ 371 (c)(1),
(2) Date: Aug. 7, 2014

(87) PCT Pub. No.: WO2013/116936
PCT Pub. Date: Aug. 15, 2013

(65) Prior Publication Data
US 2015/0010665 A1    Jan. 8, 2015

Related U.S. Application Data

(60) Provisional application No. 61/597,453, filed on Feb. 10, 2012.

(51) Int. Cl.
*A61K 36/288* (2006.01)
*A61K 45/06* (2006.01)

(52) U.S. Cl.
CPC ............ *A61K 36/288* (2013.01); *A61K 45/06* (2013.01); *A61K 2236/15* (2013.01)

(58) Field of Classification Search
None
See application file for complete search history.

(56) References Cited

PUBLICATIONS

Koo et al. (2004) Life Sciences 74, 1149-1157.*
Raskin et al. (2004) Current Pharmaceutical Design 10, 3419-3429.*
Revilla et al. (1998) J. Agric. Food Chem. 46, 4592-4597.*
Chatterjee, S.J. et al. The efficacy of dandelion root extract in inducing apoptosis in drug-resistant human melanoma cells. Evid Based Complement Alternat Med. Published Online Dec. 30, 2010. Retrieved from the Internet <URL:http//www.ncbi.nlm.nih.gov/pmc/articles/PMC3018636/> <DOI:10.1155/2011/129045>, the whole document.
Ovadje, P. et al. Selective induction of apoptosis through activation of caspase-8 in human leukemia cells (Jurkat) by dandelion root extract. J Ethnopharmacol. Jan. 7, 2011, vol. 133, No. 1, pp. 86-91, ISSN: 0378-8741, the whole document.
Ovadje P. et al. Efficient induction of extrinsic cell death by dandelion root extract in human chronic myelomonocytic leukemia (CMML) cells. PLoS One. Feb. 2012, vol. 7, issue 2,. Published Online Feb. 17, 2012. Retrieved from the Internet <URL:http://www.ncbi.nlm.nih.gov/pmc/articles/PMC3281857/><DOI:10.1371/journal.pone.0030604 >, the whole document.
Ngamnikom, P. et al. The effects of freeze, dry, and wet grinding processes on rice flour properties and their energy consumption. Journal of Food Engineering, Jun. 4, 2011, vol. 104, pp. 632-638. ISSN: 0620-8774.
Nystrom, L. et al. Effects of processing on availability of total plant sterols, steryl ferulates and steryl glycosides from wheat and rye bran. J Agric Food Chem. Oct. 31, 2007, vol. 55, No. 22, pp. 9059-6065 ISSN: 0021-8561.
Health From the Sun, Freeze-Grinding, [Retrieved on May 21, 2014] Retrieved from the Internet: <URL:http.www.healthfromthesea.us/healthcare/freeze_griding.php>.
Ovadje, P. et al. "Selective Induction of Apoptosis and Autophagy Through Treatment with Dandelion Root Extract in Human Pancreatic Cancer Cells", Pancreas, 41 (2012): 1039-1047.
Sigstedt, S.C. et al., "Evaluation of aqueous extracts of *Taraxacum officinale* on growth and invasion of breast and prostate cancer cells", International Journal of Oncology, 32 (2008): 1085-1090.
Schütz, K., "Taraxacum—A review on its phytochemical and pharmacological profile", Journal of Ethnopharmacology 107 (2006): 313-323.
Takasaki, M. et al., "Anti-carcinogenic Activity of *Taraxacum* Plant. I", Biol. Pharm. Bull. 22(6), (1999): 602-605.
Takasaki, M. et al., Anti-carcinogenic Activity of Taraxacum Plant. II, Biol. Pharm. Bull. 22(6), (1999): 606-610.

* cited by examiner

*Primary Examiner* — Christopher R Tate
*Assistant Examiner* — Russell G Fiebig

(57) ABSTRACT

The present invention relates to an improved method for preparing a medicament comprising a *Taraxacum* plant root extract for the treatment or prevention of a cancer. In one aspect, the method comprises freezing *Taraxacum* plant root to obtain a frozen root stock, said freezing step being selected to effect at least partial disruption of one or more root cells; dry grinding the frozen root stock to obtain a ground root powder, wherein during said dry grinding step the frozen root stock is maintained at a grinding temperature below about 40° C.; steeping the ground root powder with a solvent to obtain a suspension having a liquid extract portion and a solid particle portion; and separating the liquid extract portion from the solid particle portion to provide a separated liquid extract for use in the medicament.

21 Claims, 34 Drawing Sheets

DRE fed

MEDICAMENT CONTAINING TARAXACUM PLANT ROOT EXTRACT FOR TREATMENT OR PREVENTION OF CANCER, AND METHOD FOR PREPARING SAME

RELATED APPLICATIONS

This application claims the benefit of 35 U.S.C. 119(e) to U.S. Provisional Patent Application Ser. No. 61/597,453 filed on 10 Feb. 2012.

SCOPE OF THE INVENTION

The present invention relates to an improved method of preparing a medicament which includes a root extract of plants belonging to the genus *Taraxacum*, and which is for treatment, amelioration or prevention of cancers. More particularly, the present invention relates to the preparation of a pharmaceutical composition which includes *Taraxacum* plant root extracts for use in the treatment and/or prevention of cancers, and preferable colon cancers, pancreatic cancer, skin cancers such as melanoma, and blood cancers such as chronic lymphoid leukemia, chronic myeloid leukemia, chronic monocytic myeloid leukemia and Hodgkin's lymphoma.

BACKGROUND OF THE INVENTION

Plants of the genus *Taraxacum*, also commonly known as dandelions, are members of the Asteraceae family. These plants are commonly found in temperate zones of the Northern Hemisphere, and species of dandelions include *T. officinale*, *T. erythrospermum*, *T. albidum*, *T. japonicum*, *T. laevigatum*, *T. erythrospermum* and *T. californicum*.

Dandelions are tap-rooted biennial or perennial herbaceous plants with an average length of 15 to 30 cm. The leaves are large, light to dark green in color and cluster in a rosette at the base of the plant. The flowering stalks are upstanding and carries a solitary, terminal inflorescence. The florescence ranges from 7 to 15 mm in diameter and is composed of 140 to 400 yellow, ligulate florets. The fruits are conical achenes, brown and crowned by a white, hairy papus, which allows the seeds to be distributed by wind over long distances.

*Taraxacum* plant roots often contain a variety of compounds including sesquiterpenes, carotenoids, coumarins, flavonoids, phenolic acids, polysaccharides, eudesmanolides, triterpenes, sterols, steroids and others. Specific examples of such compounds include germacranolide, eudesmanolide, guaianolide, taraxacin, phenylpropanoid glycosides, taraxacoside, lactupircin, lutein, violaxanthin, esculin, scopoletin, quercetin, luteolin, rutin, chrysoeriol, caffeic acid, vanillic acid, syringic acid, ferulic acid, chlorogenic acid, chicoric acid, ρ-hydroxyphenylacetic acids, p-hydroxylbenzoic acid, inulin, glucans, mannans, prunasin, 11β, 13-dihydrolactucin, ixerin D, ainslioside taraxinic acid, β-glucopyranosyl, taraxinic acid, glucosyl ester, 11, 13-dihydrotaraxinic acid, 1'-glucoside, lactucopicrin, lactucin, cichorin, tetrahydroridentin B, taraxacolide-O-β-glucopyranoside, prunasin, dihydroconiferin, syringin, dihydrosyringin, taraxasterol, ψ-taraxasterol, homo-taraxasterol, stigmatsterol, cycloartenol, umbelliferone, taraxalisin, α-amyrin, β-amyrin, arnidiol, faradiol, lupeol, taraxol, taraxaserol, 3β-hydroxylup-18-ene-21-one, β-sitosterol, campesterol, lettucenin A, choline, mucilage, pectin, and taraxerol.

Dandelion extracts have been used in the past as for example antioxidants, diuretics, analgesics, anti-coagulants and anticancer agents. The publication "Evaluation of aqueous extracts of *Taraxacum officinale* on growth and invasion of breast and prostate cancer cells" *International Journal of Oncology* 32 (2008): 1085-1090 to Sigstedt reports on the anticancer activity of crude extracts prepared from the leaves ("DLE"), flowers ("DFE") or roots ("DRE") of the dandelion species *Taraxacum officinale*. The crude dandelion extracts in Sigstedt were prepared by 1) soaking 75 g of dried plant parts in water for 24 hours at room temperature; 2) filtering the resulting mixture to remove particulate matter; and 3) lyophilizing the mixture to obtain a powder. Sigstedt observes that DLE reduced the growth of MCF-7/AZ breast cancer cells, and not that of LNCaP C4-2B prostate cancer cells; and that both DFE and DRE failed to influence cancer cell proliferation.

The publication "Anti-carcinogenic Activity of *Taraxacum* Plant. I" *Biol. Pharm. Bull.* 22.6 (1999): 602-605 to Takasaki relates to dandelion root extracts prepared from the species *Taraxacum japonicum*. Takasaki describes extracting dried roots (600 g) of *T. japonicum* plant three times with 3 L of methanol for five hours each, and then evaporating the methanol solution to afford 109 g of a methanol extract. Takasaki additionally describes the preparation of a water extract obtained from extracting 60 g of *T. japonicum* roots with 0.38 L of water for 1 hour, and then lyophilizing the resulting solution. Takasaki describes that the methanol and water extracts inhibited initiation and promotion of two-stage chemical carcinogenesis.

In the separate publication "Anti-carcinogenic Activity of *Taraxacum* Plant. II" *Biol. Pharm. Bull.* 22.6 (1999): 606-610, Takasaki describes another dandelion root preparation of *T. japonicum* obtained from extracting dried roots (6.7 kg) with 40 L of n-hexane three times for 8 hours each to produce a 120.5 g extract.

Dandelion plant parts have been utilized to prepare extracts in various forms including capsules and tinctures. Dandelion roots in particular have been harvested for preparing "dandelion coffee" obtained by steeping dried ground plant root in boiling water. It has been appreciated that such conventional forms of dandelion extracts are ordinarily associated with lower anticancer activities, inducing as low as 10% cell death when introduced to a cancerous or tumor tissue.

SUMMARY OF THE INVENTION

It is an object of the present invention to provide a medicament or pharmaceutical composition for the treatment, amelioration and/or prevention of cancers, and which includes a *Taraxacum* plant root extract, preferably in combination with a pharmaceutically acceptable carrier, a diluent, a binding agent, an adjuvant and/or other anticancer agents.

A further object of the present invention is to provide a *Taraxacum* plant root extract which is suitable and/or beneficial for use as a medicament or human consumption.

A yet further object of the present invention is to provide a method of preparing a medicament or pharmaceutical composition having a *Taraxacum* plant root extract which includes one or more compounds useful for the treatment, amelioration and/or prevention of a cancer.

It has been appreciated that a *Taraxacum* plant root extract may be useful in the treatment and/or prevention of cancers, and which may include without restriction pancreatic cancers, colon cancers, blood cancers and skin cancers. Such skin cancers may be melanoma, and such blood cancers may be leukemia, such as but not limited to Hodgkin's lymphoma, chronic lymphoid leukemia, chronic myeloid leukemia and chronic monocytic myeloid leukemia.

In one possible method, a medicament for the treatment or prevention of a cancer may be prepared by: freezing *Taraxacum* plant root to obtain a frozen root stock, said freezing step being selected to effect at least partial disruption of one or more root cells; dry grinding the frozen root stock to obtain a ground root powder, wherein during said dry grinding step the frozen root stock is maintained at a grinding temperature below about 40° C.; steeping the ground root powder with a solvent to obtain a suspension having a liquid extract portion and a solid particle portion; and separating the liquid extract portion from the solid particle portion to provide a separated liquid extract for use in the medicament.

Although not intended to be bound by theory, it was experimentally shown that anticancer compounds contained in a *Taraxacum* plant root may undergo a reduction in their activities if subject to an elevated temperature in a dry environment, although such effect is less pronounced or absent in wet environments. The applicant has recognized that during an extract preparation process, a *Taraxacum* plant root may unfavorably be left exposed to dry heat, resulting in the reduction and possibly elimination of anticancer activities. A *Taraxacum* plant root and its anticancer activity may be most vulnerable to the deactivating effects of dry heat during the grinding step where the plant roots, root cells and cellular contents could be heated on contact with a rotating element of a grinder, such as a grinder blade. A number of experiments were performed to show that loss of activities could occur above 40° C., and a complete loss of anticancer activities may result from exposure to a temperature above 70° C.

In a preferred embodiment, the grinding temperature is kept below about 0° C., more preferably below about −25° C., and most preferably below about 40° C.

Furthermore, it has been appreciated that the anticancer activity of medicament having a *Taraxacum* plant root extract may be improved if prepared with ground plant root obtained from dry grinding rather than wet grinding. Dry grinding is believed to provide improved and/or more controllable disruption of root cells, and thus greater amounts of intracellular anticancer contents or compounds available for subsequent extraction steps. Preferably, the frozen root stock is dry ground to an average particle size of less than about 100 μm, more preferably less than about 50 μm and most preferably between about 1 μm and about 30 μm.

In a preferred aspect, a *Taraxacum* root extract may be especially useful for inclusion in a medicament for the treatment, amelioration or prevention of cancers when prepared with dandelion roots obtained from dormant *Taraxacum* plants harvested before, or more preferably within about 90 days, and most preferably about 30 days prior to plant blooming or budding in the spring season, or before entering dormancy in the winter season when bud growth ceases.

Although not intended to be bound by theory, it is believed that *Taraxacum* plant roots undergo physiological changes in preparation of blooming or dormancy. Specifically, based on the experimental results obtained from the extracts prepared from dandelion roots ("DRE") obtained at three different time points (Spring, Summer and beginning of Fall), the extracts prepared from the roots harvested in early spring and beginning of the fall period were shown to be the most effective in inducing cell death in cancer cells.

In particular, dandelion roots harvested in the province of Ontario, Canada in March, September and October were shown to be highly effective in inducing apoptosis of cancer cells. It is believed that the anticancer compounds in the root extract are synthesized in preparation for dormancy (during the cold weather), and which may be involved in inducing cell death and eliminating the aged cells in the plant in preparation for winter.

In a preferred embodiment, the *Taraxacum* plant root is, prior to the freezing step, dried to a relative humidity of about 5% to 10%. Preferably the plant root is diced into root pieces, which may have an average dimension between about 0.2 cm and 1.0 cm.

The *Taraxacum* plant root is preferably obtained from a *Taraxacum* species including but not limited to *T. officinale, T. erythrospermum, T. albidum, T. japonicum, T. laevigatum, T. erythrospermum* and *T. californicum*. Most preferably, the plant root is harvested from *T. officinale* or *T. laevigatum* collected from an open grassy area.

Preferably in the freezing step the plant root is contacted or submerged in liquid nitrogen, or alternatively, subjected to a freezing temperature below 0° C., or more preferably between about −210° C. and about −30° C., for about 5 minute to 24 hours or until substantially frozen.

The dry grinding step may be carried out with a grinder, including but not limited to a mortar and pestle, a pulverizer, an impingement grinder and a micronized milling machine to effect substantial disruption of root cells. To reduce exposure to elevated temperatures in a dry environment above 40° C., the grinder is preferably cooled, with for example liquid nitrogen, to prevent heating on contact with the frozen root stock or the resulting ground root powder. Preferably, the grinder is cooled below about −25° C., and more preferably below about −50° C.

To better effect the release of therapeutically active compounds located inside the root cells, the grinding step is most preferably performed to disrupt or break open the cells and release their inner contents.

The ground root powder is steeped or soaked in a liquid or solvent, preferably in a polar solvent, such as water at a soaking temperature between about 5° C. and about 100° C., or most preferably at about 25° C. Other suitable solvents include but not limited to pentane, cyclopentane, cyclohexane, benzene, toluene, 1,4-dioxane, chloroform, diethyl ether, dichloromethane, tetrahydrofuran, ethyl acetate, acetone, dimethylformamide, acetonitrile, dimethyl sulfoxide, propylene carbonate, formic acid, n-butanol, isopropanol, n-propanol, ethanol, methanol and acetic acid. The ground root powder is preferably soaked in the liquid between about 5 minutes to about 24 hours, or more preferably between about 10 minutes and about 30 minutes with or without stirring. Most preferably, the ground root powder is soaked in water at 10 g ground root 50 mL water, and is boiled between 10 minutes and 30 minutes.

The liquid extract portion of the suspension may be separated from the solid particle portion preferably by filtration and/or centrifugation. Preferably, centrifugation, if performed, is carried out between 5000× g to 8000× g to remove any excess fibers. Filtration is preferably performed using suction filtration and a paper filter. The paper filter preferably has the pore size of less than or equal to about 0.45 μm, and most preferably less than or equal to about 0.22 μm. In a most preferred embodiment, the filtration step is performed stepwise using paper filters of decreasing pore sizes (such as 0.45 μm filter, followed by 0.22 μm filter). One or more filters or filter papers utilized for the filtration step may be configured to remove a bacteria.

The separated liquid extract obtained from the suspension is preferably freeze dried to an extract powder. Preferably, the freeze drying step is performed at a temperature between about −80° C. and −40° C.

The extract powder may be included in the medicament together with a pharmaceutically acceptable carrier, a diluent, a binding agent, an adjuvant and/or additionally anticancer agents. Such anticancer agents may include metformin, hydroxyurea, cyclophosphamide and/or etoposide.

The medicament preferably include a dosage form which contains the extract powder in a range about 5 mg/kg weight/day to about 1000 mg/kg weight/day, and preferably about 10 mg/kg weight/day to about 70 mg/kg weight/day. Alternatively, 0.2 to 200 g, preferably about 0.5 g to about 70 g, and most preferably about 1 to 4 g of the extract powder is preferably included in medicament form as a daily dosage.

In yet another aspect, the present invention provides a method for preparing a medicament comprising a *Taraxacum* plant root extract for treatment or prevention of a cancer, the method comprising the steps of: (1) freezing *Taraxacum* plant root to obtain a frozen plant root stock, said freezing step selected to effect at least partial disruption of one or more root cells, wherein said *Taraxacum* plant root comprises a dormant *Taraxacum* plant root harvested either prior to plant budding or blooming, or after cessation of bud growth; (2) dry grinding said frozen plant root stock to obtain a ground plant root powder with an average particle size of less than about 100 μm, and preferably less than about 50 μm, wherein during said dry grinding step the frozen root stock is maintained at a grinding temperature below about 40° C.; (3) soaking the ground plant root powder in a solvent comprising one or both of ethanol and water to produce a mixture having a liquid solution portion and a solid portion; (4) separating the liquid solution portion from the solid portion; and (5) freeze drying the liquid solution portion to obtain the *Taraxacum* plant root extract as a dried extract powder, and optionally mixing the dried extract portion with one or more of a pharmaceutically acceptable carrier, a diluent, a binding agent, an adjuvant and an anticancer agent.

The dormant plant root is harvested within 90 days, and preferably about 30 days, prior to first seasonal plant blooming or budding. The plant root may be from a plant belonging to a species of *T. officinale, T. erythrospermum, T. albidum, T. japonicum, T. laevigatum, T. erythrospermum* and *T. californicum.*

The plant root is preferably dried to a relative humidity of less than about 10% before freezing. In the following freezing step, the plant root is preferably contacted or submerged in liquid nitrogen to an average freezing temperature between about −210° C. and about −30° C.

In the dry grinding step, the frozen root stock is ground preferably to an average particle size of less than about 50 μm, and more preferably between about 1 μm to about 30 μm. The dry grinding step may be carried out with a grinder, including but not limited to a mortar and pestle, a pulverizer, an impingement grinder and a micronized milling machine to effect substantial disruption of one or more root cells. To reduce exposure to elevated temperatures in a dry environment, the grinder is preferably cooled, with for example liquid nitrogen, to a temperature below about −25° C., and preferably below about −50° C.

The solvent for use in the soaking step may additionally include one or more of pentane, cyclopentane, cyclohexane, benzene, toluene, 1,4-dioxane, chloroform, diethyl ether, dichloromethane, tetrahydrofuran, ethyl acetate, acetone, dimethylformamide, acetonitrile, dimethyl sulfoxide, propylene carbonate, formic acid, n-butanol, isopropanol, n-propanol, methanol or acetic acid. The soaking step is most preferably performed at a soaking temperature between about 5° C. and about 100° C., preferably for a period of about 5 minutes to about 24 hours, with or without stirring.

Various techniques may be utilized for separating the liquid solution portion from the solid portion in the mixture. Such techniques may include but not limited to centrifugation and filtration. Centrifugation, if performed, is preferably carried out between 5000× g to 8000× g. Filtration, if used, is most preferably performed at least twice using at least two filters of different pore sizes, such as about 0.45 μm and about 0.22 μm. For improved safety for human consumption, one or more filters or filter papers utilized for the filtration step may be configured to remove a bacteria.

In a preferred embodiment, the grinding temperature is below about 0° C., more preferably below about −25° C., and most preferably below about −40° C.

The medicament preferably include a dosage form which contains the *Taraxacum* plant root extract in a range about 5 mg/kg weight/day to about 1000 mg/kg weight/day, and preferably about 10 mg/kg weight/day to about 70 mg/kg weight/day. Alternatively, about 0.5 g to about 70 g, and preferably about 1 to 4 g of the *Taraxacum* plant root extract is preferably included in the medicament in a daily dosage form.

In aspect (1), the present invention provides a method for preparing a medicament for the treatment or prevention of a cancer, the method comprising: freezing *Taraxacum* plant root to obtain a frozen root stock, said freezing step being selected to effect at least partial disruption of one or more root cells; dry grinding the frozen root stock to obtain a ground root powder, wherein during said dry grinding step the frozen root stock is maintained at a grinding temperature below about 40° C.; steeping the ground root powder with a solvent to obtain a suspension having a liquid extract portion and a solid particle portion; and separating the liquid extract portion from the solid particle portion to provide a separated liquid extract for use in the medicament.

In aspect (2), the current invention provides a method according to aspect (1), wherein said cancer is a colon cancer, a pancreatic cancer, a blood cancer or a skin cancer.

In aspect (3), the present invention provides a method according to aspect (1) and/or (2), wherein said cancer comprises said blood cancer or said skin cancer, and is selected from the group consisting of chronic lymphoid leukemia, chronic myeloid leukemia, chronic monocytic myeloid leukemia, Hodgkin's lymphoma, and melanoma.

In aspect (4), the present invention provides a method according to any one or more of aspects (1) to (3) in any combination, wherein prior to said freezing step, the method further comprises drying said plant root to a relative humidity between about 5% to about 10%.

In aspect (5), the present invention provides a method according to any one or more of aspects (1) to (4) in any combination, wherein said *Taraxacum* plant root comprises a dormant *Taraxacum* plant root harvested either prior to plant blooming or budding, or after cessation of bud growth.

In aspect (6), the present invention provides a method according to any one or more of aspects (1) to (5) in any combination, wherein said dormant *Taraxacum* plant root is harvested within about 90 days, and preferably about 30 days, prior to said plant blooming or budding.

In aspect (7), the present invention provides a method according to any one or more of aspects (1) to (6) in any combination, wherein said *Taraxacum* plant root is from a plant belong to a species selected from the group consisting of *T. officinale, T. erythrospermum, T. albidum, T. japonicum, T. laevigatum, T. erythrospermum* and *T. californicum.*

In aspect (8), the present invention provides a method according to any one or more of aspects (1) to (7) in any combination, wherein said freezing step comprises contacting or submerging the plant root in liquid nitrogen, or freezing the plant root to an average freezing temperature between about −210° C. and about −30° C.

In aspect (9), the present invention provides a method according to any one or more of aspects (1) to (8) in any combination, wherein said dry grinding step comprises dry grinding the frozen root stock to an average particle size of less than about 100 μm, and preferably less than about 50 μm.

In aspect (10), the present invention provides a method according to any one or more of aspects (1) to (9) in any combination, wherein said dry grinding step comprises dry grinding the frozen root stock with a grinder selected from the group consisting of a pulverizer, an impingement grinder and a micronized milling machine, and wherein the grinder or a component thereof is cooled below about −25° C., and preferably below about −50° C., to prevent heating on contact with the frozen root stock or the ground root powder.

In aspect (11), the present invention provides a method according to any one or more of aspects (1) to (10) in any combination, wherein said solvent comprises one or more of water, pentane, cyclopentane, cyclohexane, benzene, toluene, 1,4-dioxane, chloroform, diethyl ether, dichloromethane, tetrahydrofuran, ethyl acetate, acetone, dimethylformamide, acetonitrile, dimethyl sulfoxide, propylene carbonate, formic acid, n-butanol, isopropanol, n-propanol, ethanol, methanol and acetic acid.

In aspect (12), the present invention provides a method according to any one or more of aspects (1) to (11) in any combination, wherein said steeping step comprises soaking the ground root powder in water at a soaking temperature between about 2° C. and about 150° C., and preferably 5° C. and 100° C., preferably for a period of about 5 minutes to about 24 hours, with or without stirring.

In aspect (13), the present invention provides a method according to any one or more of aspects (1) to (12) in any combination, wherein said separation step comprises at least one of filtration and centrifugation, and wherein the filtration is performed once or more than once using a plurality of filters of same or different pore sizes, and the centrifugation is performed at 5000 × g to 8000 × g.

In aspect (14), the present invention provides a method according to any one or more of aspects (1) to (13) in any combination, wherein said separation step comprises filtering the suspension at least twice with a first filter having a first pore size of about 0.45 μm and a second filter having a second pore size of about 0.22 μm, and wherein the second filter is selected to remove a bacteria.

In aspect (15), the present invention provides a method according to any one or more of aspects (1) to (14) in any combination, wherein prior to the dry grinding step, the method further comprises dicing said plant root to produce a plurality of root pieces.

In aspect (16), the present invention provides a method according to any one or more of aspects (1) to (15) in any combination, wherein said grinding temperature is below about 0° C.

In aspect (17), the present invention provides a method according to any one or more of aspects (1) to (16) in any combination, wherein said grinding temperature is below about −25° C., and preferably below about −40° C.

In aspect (18), the present invention provides a method according to any one or more of aspects (1) to (17) in any combination, wherein said method further comprises freeze drying the separated liquid extract to obtain an extract powder, and optionally mixing the extract powder with one or more of a pharmaceutically acceptable carrier, a diluent, a binding agent, an adjuvant and an anticancer agent.

In aspect (19), the present invention provides a method according to any one or more of aspects (1) to (18) in any combination, wherein said anticancer agent is one or more of metformin, hydroxyurea, cyclophosphamide and etoposide.

In aspect (20), the present invention provides a method according to any one or more of aspects (1) to (19) in any combination, wherein said medicament comprises a dosage form having the extract powder in a range of about 5 mg/kg weight/day to about 1000 mg/kg weight/day, and preferably about 10 mg/kg weight/day to about 70 mg/kg weight/day.

In aspect (21), the present invention provides a method according to any one or more of aspects (1) to (20) in any combination, wherein said medicament comprises a daily dosage form having the extract powder in a range of about 0.5 g to about 70 g, and preferably about 1 to 4 g.

In aspect (22), the present invention provides a method for preparing a medicament comprising a *Taraxacum* plant root extract for treatment or prevention of a cancer, the method comprising the steps of: (1) freezing *Taraxacum* plant root to obtain a frozen plant root stock, said freezing step selected to effect at least partial disruption of one or more root cells, wherein said *Taraxacum* plant root comprises a dormant *Taraxacum* plant root harvested either prior to plant budding or blooming, or after cessation of bud growth; (2) dry grinding said frozen plant root stock to obtain a ground plant root powder with an average particle size of less than about 100 μm, and preferably less than about 50 μm, wherein during said dry grinding step the frozen root stock is maintained at a grinding temperature below about 40° C.; (3) soaking the ground plant root powder in a solvent comprising one or both of ethanol and water to produce a mixture having a liquid solution portion and a solid portion; (4) separating the liquid solution portion from the solid portion; and (5) freeze drying the liquid solution portion to obtain the *Taraxacum* plant root extract as a dried extract powder, and optionally mixing the dried extract portion with one or more of a pharmaceutically acceptable carrier, a diluent, a binding agent, an adjuvant and an anticancer agent.

In aspect (23), the present invention provides a method according to aspect (22), wherein said cancer is a colon cancer, a pancreatic cancer, a blood cancer or a skin cancer.

In aspect (24), the present invention provides a method according to aspect (22) and/or (23), wherein said cancer is chronic lymphoid leukemia, chronic myeloid leukemia, chronic monocytic myeloid leukemia, Hodgkin's lymphoma, or melanoma.

In aspect (25), the present invention provides a method according to any one or more of aspects (22) to (24) in any combination, wherein said dormant *Taraxacum* plant root is harvested within about 90 days, and preferably about 30 days, prior to first seasonal plant blooming or budding.

In aspect (26), the present invention provides a method according to any one or more of aspects (22) to (25) in any combination, wherein said *Taraxacum* plant root is from a plant belonging to a species selected from the group consisting of *T. officinale, T. erythrospermum, T. albidum, T. japonicum, T. laevigatum, T. erythrospermum* and *T. californicum.*

In aspect (27), the present invention provides a method according to any one or more of aspects (22) to (26) in any combination, wherein prior to said freezing step, the method further comprises drying said plant root to a relative humidity less than about 10%.

In aspect (28), the present invention provides a method according to any one or more of aspects (22) to (27) in any combination, wherein said freezing step comprises contacting or submerging the plant root in liquid nitrogen to an average freezing temperature between about −210° C. and about −30° C.

In aspect (29), the present invention provides a method according to any one or more of aspects (22) to (28) in any combination, wherein said dry grinding step comprises dry grinding the frozen root stock with a grinder to the average particle size of less than about 50 µm, and to effect substantial disruption of said one or more root cells, the grinder being selected from the group consisting of a pulverizer, an impingement grinder and a micronized milling machine, and wherein said dry grinding step further comprises cooling said grinder to a temperature below about −25° C.

In aspect (30), the present invention provides a method according to any one or more of aspects (22) to (29) in any combination, wherein said solvent further comprises pentane, cyclopentane, cyclohexane, benzene, toluene, 1,4-dioxane, chloroform, diethyl ether, dichloromethane, tetrahydrofuran, ethyl acetate, acetone, dimethylformamide, acetonitrile, dimethyl sulfoxide, propylene carbonate, formic acid, n-butanol, isopropanol, n-propanol, methanol or acetic acid.

In aspect (31), the present invention provides a method according to any one or more of aspects (22) to (30) in any combination, wherein said soaking step comprises soaking the ground plant root powder in the solvent at a soaking temperature between about 5° C. and about 100° C., preferably for a period of about 5 minutes to about 24 hours, with or without stirring.

In aspect (32), the present invention provides a method according to any one or more of aspects (22) to (31) in any combination, wherein said separation step comprises at least one of filtration and centrifugation, and wherein the filtration is performed once or more than once using a plurality of filters of same or different pore sizes, and the centrifugation is performed at 5000× g to 8000× g.

In aspect (33), the present invention provides a method according to any one or more of aspects (22) to (32) in any combination, wherein said separation step comprises filtering the mixture at least twice with a first filter having a first pore size of about 0.45 µm and a second filter having a second pore size of about 0.22 µm, and wherein one or both said filters are selected to remove a bacteria.

In aspect (34), the present invention provides a method according to any one or more of aspects (22) to (33) in any combination, wherein the anticancer agent comprises one or more of metformin, hydroxyurea, cyclophosphamide and etoposide.

In aspect (35), the present invention provides a method according to any one or more of aspects (22) to (34) in any combination, wherein prior to the dry grinding step, the method further comprises dicing said *Taraxacum* plant roots to produce a plurality of root pieces having an average dimension selected at between about 0.2 cm to 1.5 cm.

In aspect (36), the present invention provides a method according to any one or more of aspects (22) to (35) in any combination, wherein said grinding temperature is below about 0° C.

In aspect (37), the present invention provides a method according to any one or more of aspects (22) to (36) in any combination, wherein said grinding temperature is below about −25° C., and preferably below about −40° C.

In aspect (38), the present invention provides a method according to any one or more of aspects (22) to (37) in any combination, wherein said medicament comprises a dosage form having the *Taraxacum* plant root extract in a range of about 5 mg/kg weight/day to about 1000 mg/kg weight/day, and preferably about 10 mg/kg weight/day to about 70 mg/kg weight/day.

In aspect (39), the present invention provides a method according to any one or more of aspects (22) to (38) in any combination, wherein said medicament comprises a daily dosage form having the *Taraxacum* plant root extract in a range of about 0.5 g to about 70 g, and preferably about 1 to 4 g.

DETAILED DESCRIPTION OF THE PREFERRED EMBODIMENTS

Figure 1:
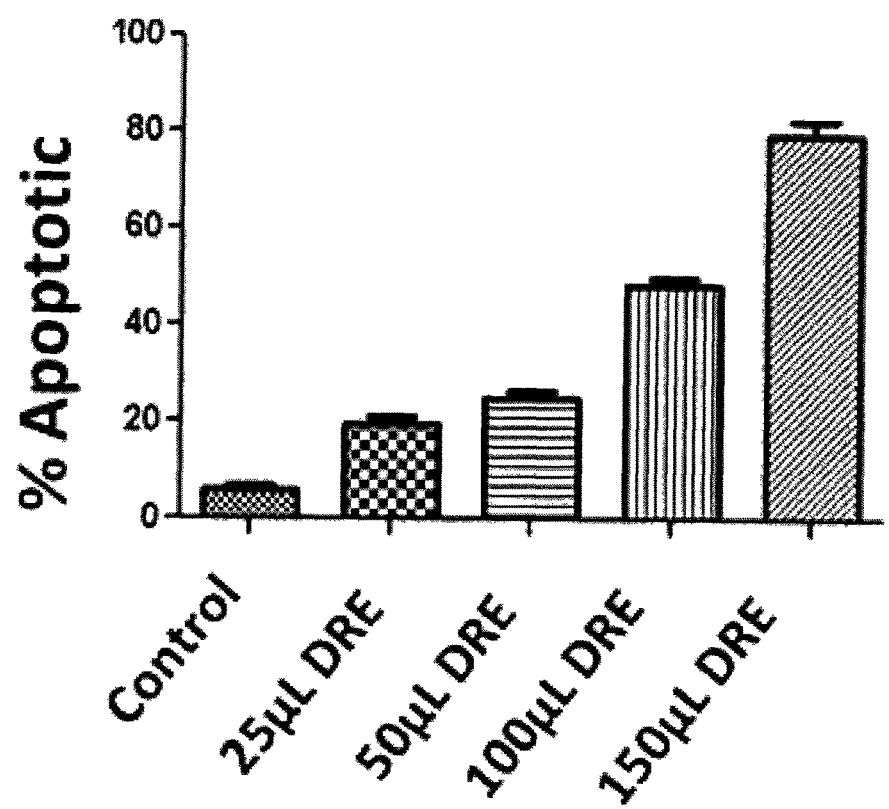
FIG. 1 is a bar graph showing the percentage of human acute T-cell leukemia (Jurkat) cells induced to apoptosis (y-axis) upon treatment with DRE of varying amounts (x-axis).

A *Taraxacum* plant root extract for use in the treatment and/or prevention of a cancer, and in accordance with a preferred embodiment of the present invention, was prepared. To prepare the preferred *Taraxacum* plant root extract, dandelions of the species *T. officinale* were collected in Ontario, Canada about 30 days prior to blooming in the spring season and right at the beginning of the fall season. The collected plants were washed in water and then cut at the base of the stem to harvest the roots. The harvested roots were then sliced lengthwise into pieces of approximately ¼" in length.

The cut root pieces were immersed in liquid nitrogen for about 5 to 10 minutes until thoroughly frozen. The frozen pieces were ground up in an impingement grinder to an average particle size of about ≤45 µm. The ground root was soaked in boiled distilled water for an hour to extract and solubilize the active compounds.

Following the extraction/solubilization step, the distilled water containing the active compounds was vacuum filtered using a paper filter with a pore size of about 0.45 µm to remove other plant matters and excess fibers. The resulting filtrate was then freeze dried at −80° C. to obtain a powdered root extract. The dried extract was reconstituted in water to give a final concentration of 100 mg/ml stock sample. The stock sample of root extract was further vacuum filtered with a bacterial paper filter having a pore size of about 0.22 µm to sterilize and prepare the extract for use. For administration, about 1 g of the powdered root extract was resolubilized in about 10 mL of boiled water and then filtered. The filtrate was then be orally administered to a patient diagnosed with cancer. Preferably, for oral administration the ratio of powdered root extract to water should be approximately in the amount of between about 0.1 g to 50 g per 100 mL.

Several fractions of the plant root extract of the present invention were isolated and tested for bioactivity testing. Based on the mechanism of apoptosis induced by DRE, multiple compounds may be responsible for the activity either alone or together in combinations for one or more different targets. Furthermore, DRE of the present invention was shown in in vitro studies, including those performed with leukemia, colon cancer, pancreatic cancer and melanoma, to selectively induce programmed cell death types I and II in human cancer cell lines, while retaining non-cancerous cells unsusceptible to apoptosis and autophagy induction. In particular, the inventors have appreciated that DRE may induce cell death by the rapid activation of the extrinsic cell death pathway possibly by targeting the death receptors, such as for example Fas or TNF family of death receptors, on cancer cells or activating the Death Inducing Signaling Complex, as evidenced by the rapid activation of caspase-8 and the subsequent activation of caspase-3, following treatment.

Furthermore, the compounds in DRE were shown to directly target the mitochondria of cancer cells suggesting that there are components of DRE that directly interact with the mitochondria, causing its destabilization for the release of pro-apoptotic factors and the generation of reactive oxygen species. DRE is believed to contain multiple compounds that could possibly have multiple targets, and which may be present as water soluble salts, ligand analogs or other interacting/binding proteins.

The medicament of the present invention were tested with a number of cell lines for its activity and/or safety. In addition, ex vivo experiments were performed with cell lines isolated from ten different cancer patients suffering from chronic lymphoid leukemia, chronic myeloid leukemia or chronic monocytic myeloid leukemia. Blood samples collected from the patients were treated with different doses of the dandelion root extract for 48 hours. When compared to blood cell lines isolated from healthy volunteers, the dandelion root extract was shown to induce apoptosis in cell lines of chronic lymphoid leukemia, chronic myeloid leukemia and chronic monocytic myeloid leukemia Further provided below is a Table which summarizes a number of additional tests performed on other cell lines and the experimental results obtained for each tested cell line:

| Cell line designation | Name | $EC_{50}$ | Result |
|---|---|---|---|
| Jurkat E6-1 | Acute T-cell leukemia | 120 µg/ml | DRE is capable of inducing apoptosis at low concentrations in Jurkat cells |
| MV-4-11 | Chronic Myelomonocytic Leukemia | 120 µg/ml | DRE effectively induces apoptosis and pro-death autophagy in a dose and time dependent manner |
| U-937 | Acute Monocytic Leukemia | 120 µg/ml | DRE effectively induces apoptosis in a dose and time dependent manner |
| HL-60 | Acute Promyelomonocytic Leukemia | 120 µg/ml | DRE effectively induces apoptosis in APL cells |
| A375 | Melanoma | 500 µg/ml | DRE has been very effective in inducing apoptosis in drug-resistant melanoma cells. This effect is enhanced by the metabolism interfering drug, metformin |
| Panc-1 | Pancreatic cancer cell line | 500 µg/ml | DRE effectively induces apoptosis and pro-death autophagy in a dose and time dependent manner |
| BxPC-3 | Pancreatic cancer cell line | 500 µg/ml | DRE effectively induces apoptosis and pro-death autophagy in a dose and time dependent manner |
| HT-29 | Colorectal cancer cell line | 200 µg/ml | DRE is effective in inducing apoptosis in aggressive colon cancer cells |
| PBMC | Peripheral Blood Mononuclear Cells (From newly diagnosed leukemia patients | 200 µg/ml | Experiments have been done using samples from 9 patients. DRE effectively induced apoptosis in PBMCs obtained from leukemia patients in a dose and time dependent manner |

To further explicitly illustrate the effectiveness of the medicament of the present invention, detailed descriptions of exemplary experiments are provided below:

i) Anticancer Activity of Dandelion Root Extract on Human T-cell Leukemia Cells

Figure 2:
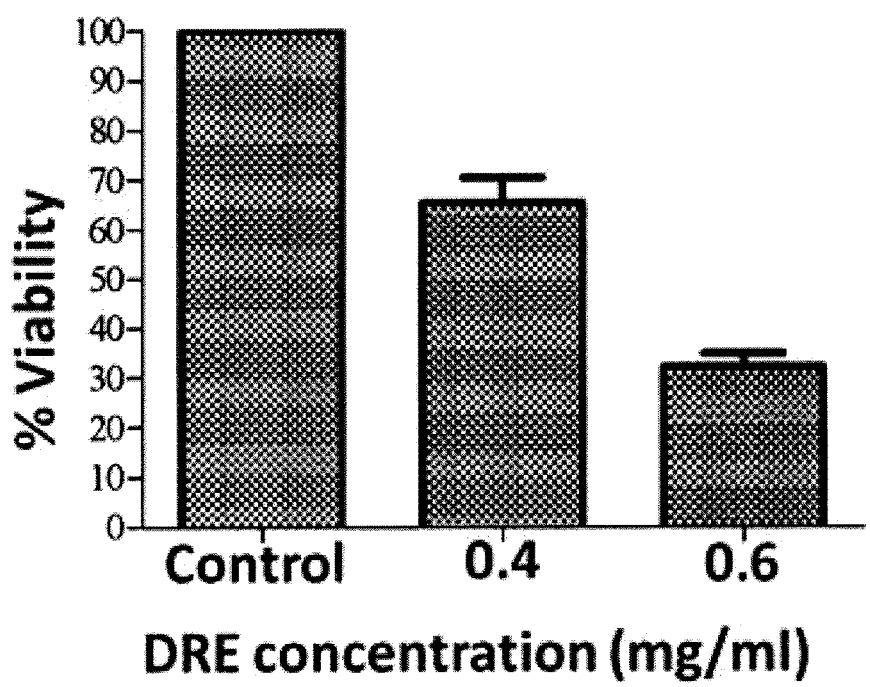
FIG. 2 is a bar graph showing the percent viability of Jurkat cells (y-axis) at varying concentrations of DRE (x-axis).
Figure 3:
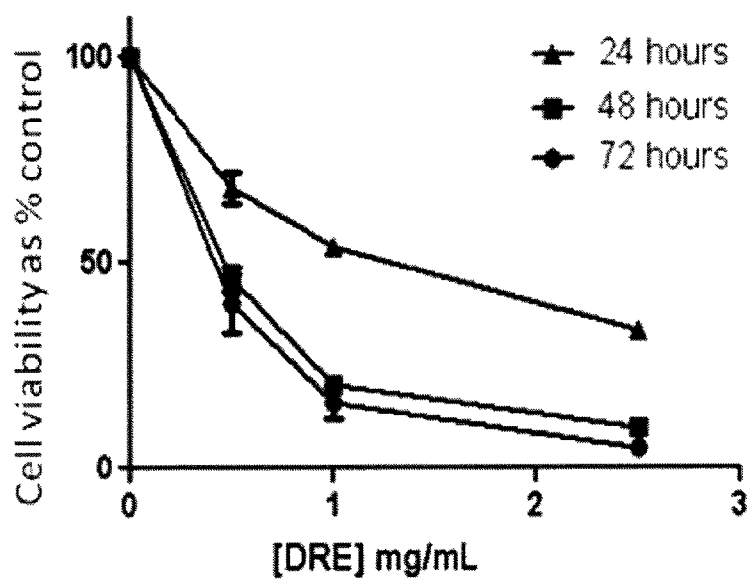
FIG. 3 is a line graph showing the percent viability of A375 human melanoma cells (y-axis) treated for 24, 48 or 72 hours with DRE of varying concentrations (x-axis).
Figure 4:
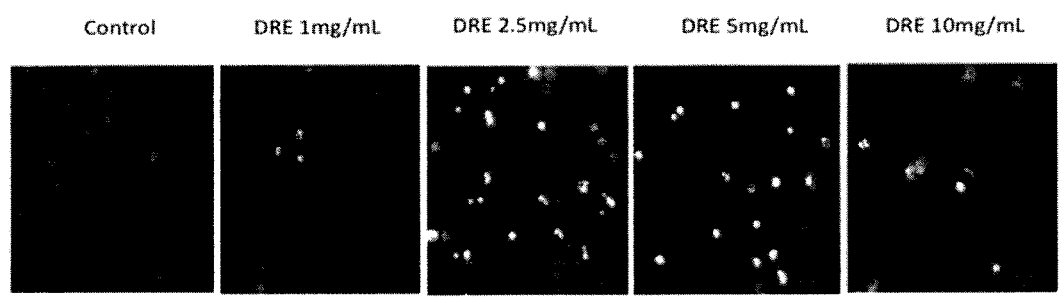
FIG. 4 is a series of fluorescence microscope images of A375 human melanoma cells stained with Hoechst 33342 dye after 48-hour treatment with DRE at concentrations of 1 mg/mL, 2.5 mg/mL, 5 mg/mL, and 10 mg/mL, and including a control.
Figure 5:
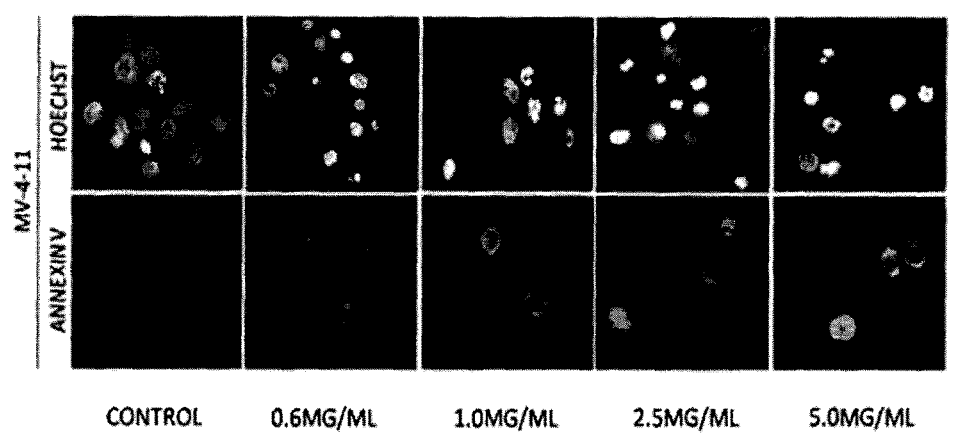
FIG. 5 is series of 400×-magnified images of MV-4-11 cells stained with Hoechst or Annexin-V stain (top and bottom rows, respectively) after 48-hour treatment with DRE at concentrations of 0.6 mg/mL, 1.0 mg/mL, 2.5 mg/mL, and 5.0 mg/mL, and including a control.
Figure 6:
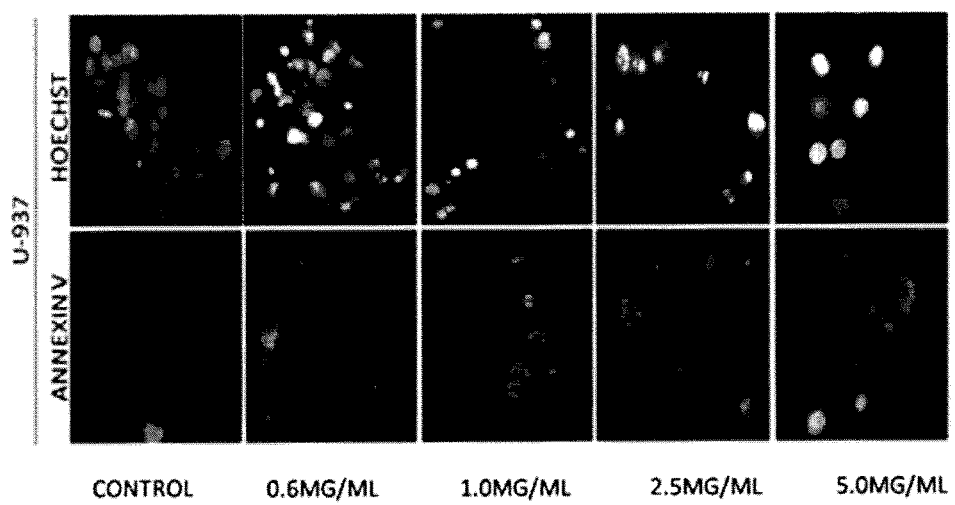
FIG. 6 is series of 400×-magnified images of U-937 cells stained with Hoechst or Annexin-V stain (top and bottom rows, respectively) after 48-hour treatment with DRE at concentrations of 0.6 mg/mL, 1.0 mg/mL, 2.5 mg/mL, and 5.0 mg/mL, and including a control.
Figure 7:
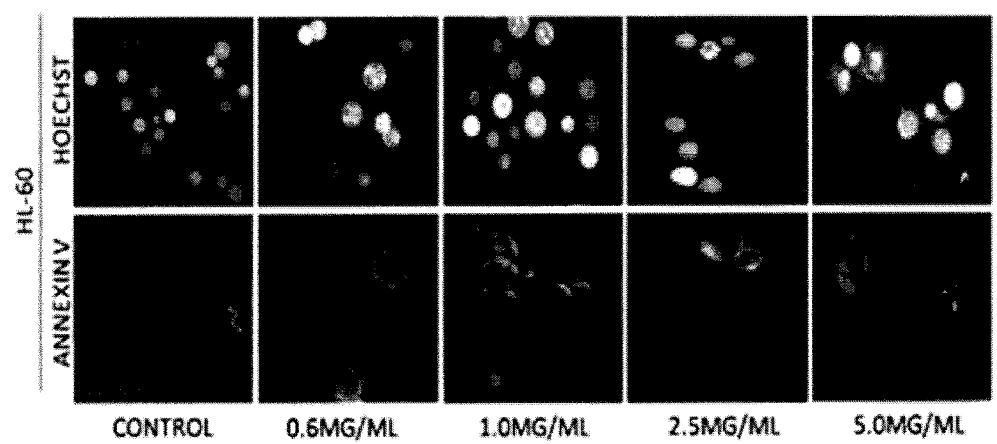
FIG. 7 is series of 400×-magnified images of HL-60 cells stained with Hoechst or Annexin-V stain (top and bottom rows, respectively) after 48-hour treatment with DRE at concentrations of 0.6 mg/mL, 1.0 mg/mL, 2.5 mg/mL, and 5.0 mg/mL, and including a control.
Figure 8:
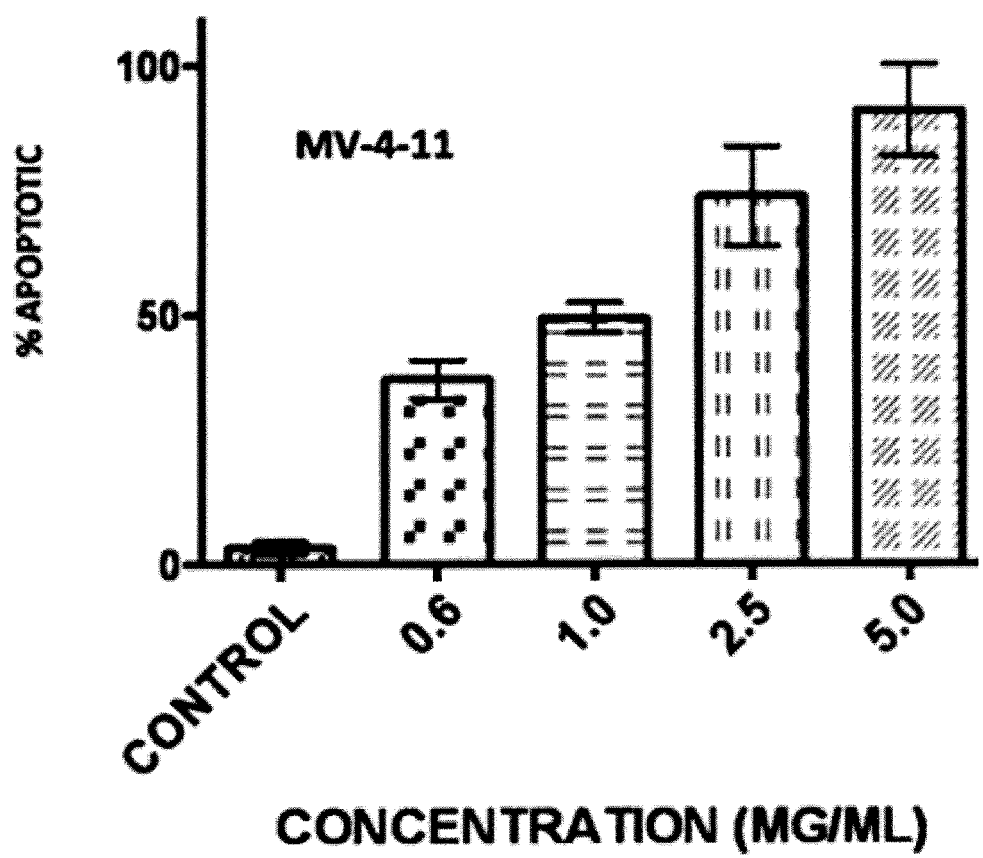
FIG. 8 is a bar graph showing the percentage of MV-4-11 cells induced to apoptosis (y-axis) after 48-hour treatment with DRE at concentrations of 0.6 mg/mL, 1.0 mg/mL, 2.5 mg/mL, and 5.0 mg/mL, and including a control.
Figure 9:
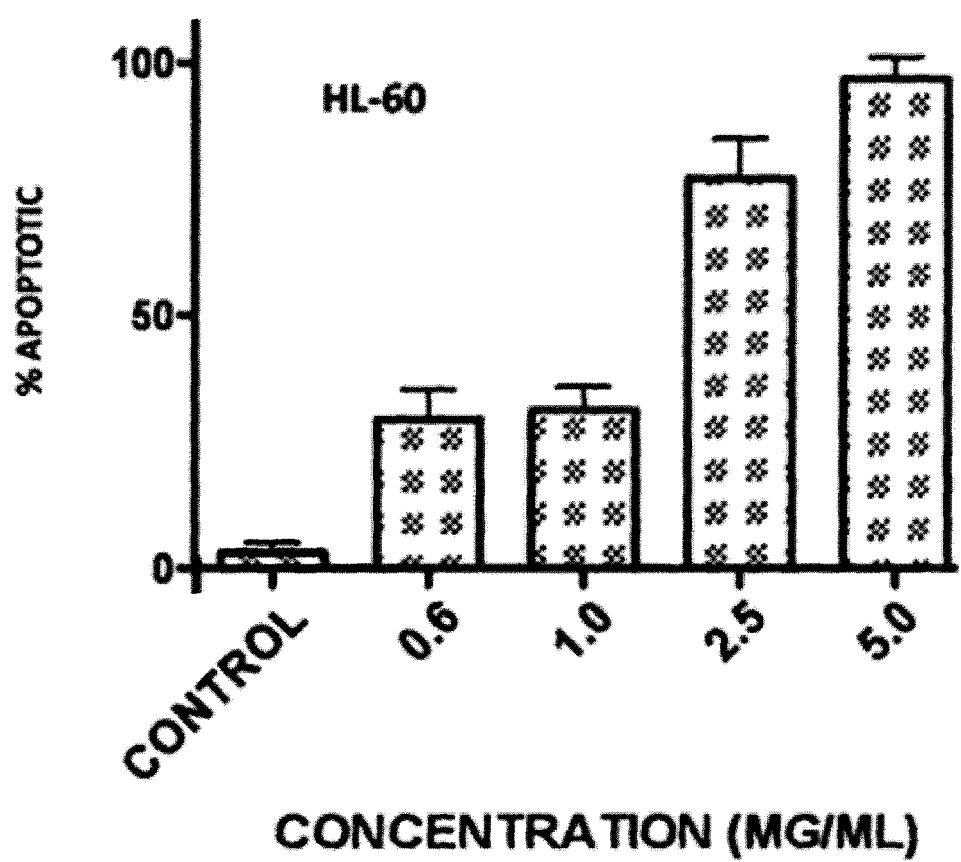
FIG. 9 is a bar graph showing the percentage of HL-60 cells induced to apoptosis (y-axis) after 48-hour treatment with DRE at concentrations of 0.6 mg/mL, 1.0 mg/mL, 2.5 mg/mL, and 5.0 mg/mL, and including a control.
Figure 10:
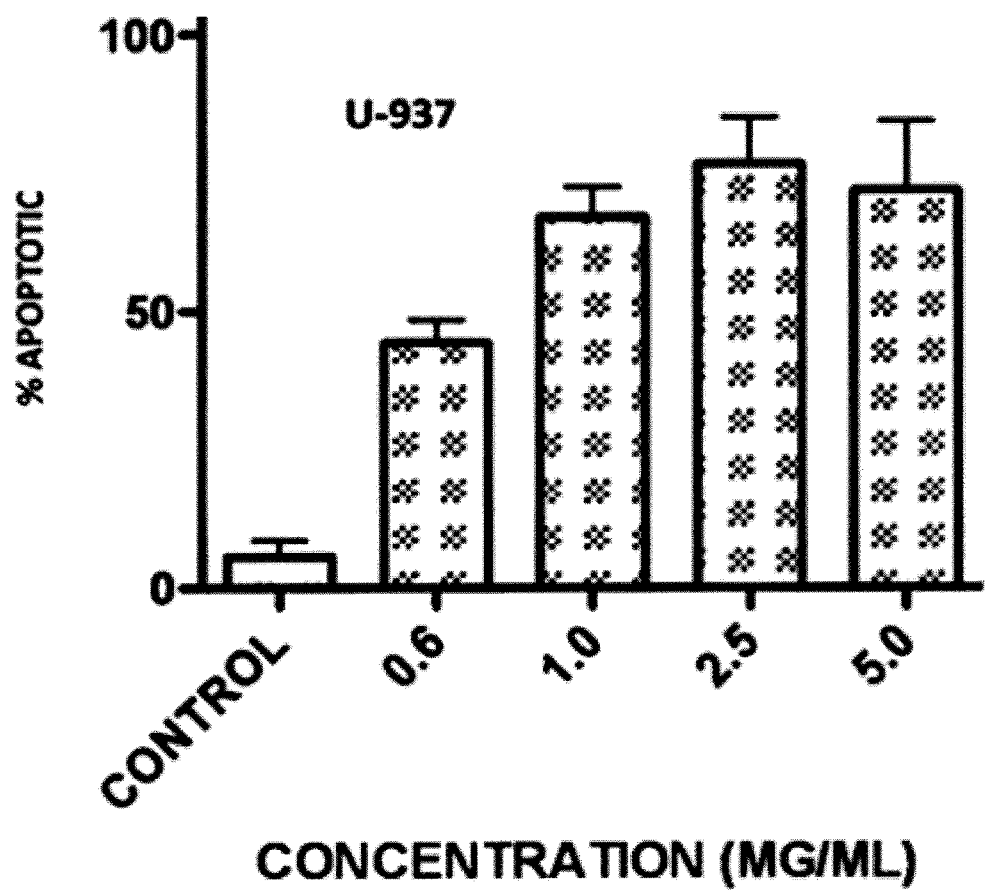
FIG. 10 is a bar graph showing the percentage of U-937 cells induced to apoptosis (y-axis) after 48-hour treatment with DRE at concentrations of 0.6 mg/mL, 1.0 mg/mL, 2.5 mg/mL, and 5.0 mg/mL, and including a control.

The activity of DRE against a human acute T-cell leukemia cell line (Jurkat) was evaluated in parallel to its effect on non-cancerous peripheral blood mononuclear cells (PBMCs). As illustrated in FIG. 1, crude dandelion extract (100 µL) induced apoptosis in approximately 50% of the cells as determined by manual counting of Hoescht images. Further, as illustrated in FIG. 2 showing the effect of DRE on the viability of Jurkat cells at 0.4 and 0.6 mg/mL as determined by WST-1 cell proliferation assay, decreased cell viability was observed with increasing concentrations of DRE. Our findings showed that DRE is capable of selectively inducing apoptosis at low concentrations specifically in cancer cells with no toxicity to PBMCs. Furthermore, it was shown that DRE treatment led to very early activation of caspase-8 and subsequent activation of caspase-3.

ii) Anticancer Activity of Dandelion Root Extract on Aggressive Human Melanoma Cells The effect of DRE on human melanoma cell lines in vitro was studied. For melanoma, a very aggressive, chemo-resistant form of skin cancer, DRE was very effective in inducing apoptosis as illustrated in FIGS. 3 and 4. To generate FIG. 3, A375 human melanoma cells were seeded on 96-well plates (about 1000 cells/well) and treated at different concentrations of DRE for 24, 48 and 72 hours. As shown in FIG. 4, typical apoptotic morphology was observed in the A375 cells treated with DRE at varying concentrations up to 10 mg/mL for 48 hours. To generate the images of FIG. 4, the cells were stained with Hoechst 33342 dye, and the images were taken on a fluorescence microscope. Brightly stained, condensed bodies indicate apoptotic nuclei.

DRE was shown to also target the mitochondria, generating reactive oxygen species. Further, drug-resistant melanoma cells were made more sensitive to DRE treatment by the metabolism interfering drug, metformin.

iii) Anticancer Activity of Dandelion Root Extract on Aggressive Human Chronic Myelomonocytic Leukemia (CMML) Cells The efficacy of DRE in more aggressive leukemia cell lines was assessed to determine its selectivity and efficacy in inducing apoptosis/autophagy in CMML cells. DRE was shown to effectively induce apoptosis and autophagy in a dose and time dependent manner as shown in FIGS. 5 to 10.

Figure 11:
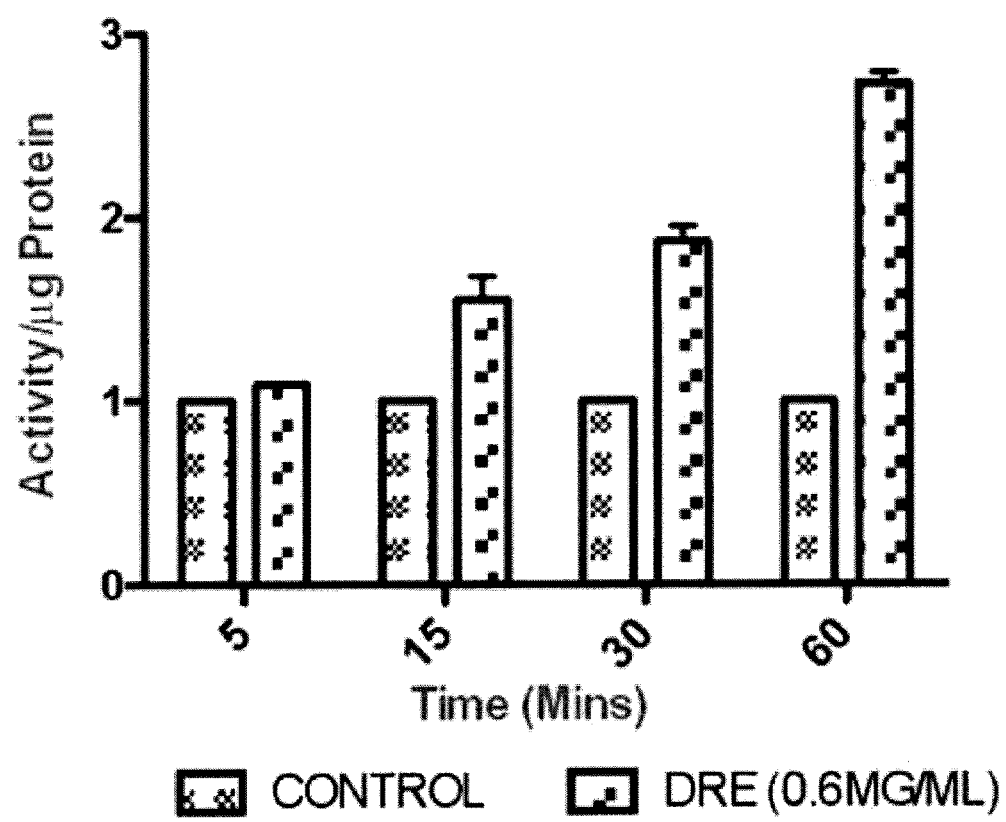
FIG. 11 is a bar graph showing activation or activity of caspase-8 in MV-4-11 cells (y-axis) 5 minutes, 15 minutes, 30 minutes and 60 minutes after treatment with 0.6 mg/mL of DRE, and including a control.
Figure 12:
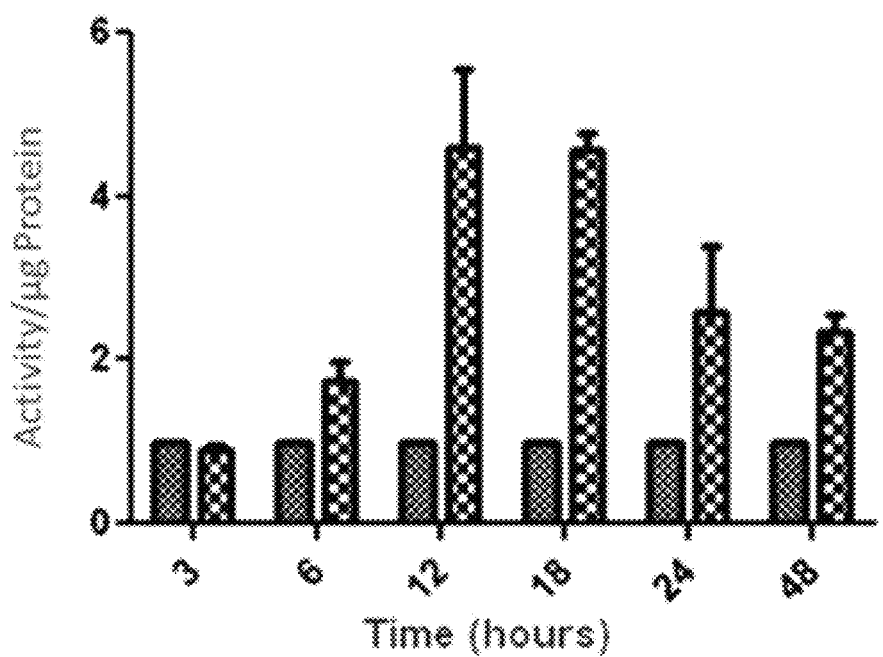
FIG. 12 is a bar graph showing activation or activity of caspase-3 in MV-4-11 cells (y-axis) 5 minutes, 15 minutes, 30 minutes and 60 minutes after treatment with 0.6 mg/mL of DRE, and including a control.

The rapid activation of caspase-8 and caspase-3 as shown in FIGS. 11 and 12 through the activation of the extrinsic pathway of apoptosis, was observed in the CMML cells, comparable to levels found in Jurkat cells. To obtain the bar graphs of FIGS. 11 and 12, MV-4-11 cells were collected following treatment with DRE at the indicated time points and DRE concentrations, washed and incubated with lysis buffer to obtain cell lysate. The cell lysate was incubated with caspase substrates specific to each caspase and incubated for an hour. Fluorescence readings were obtained using a spectrofluorometer.

Figure 17:
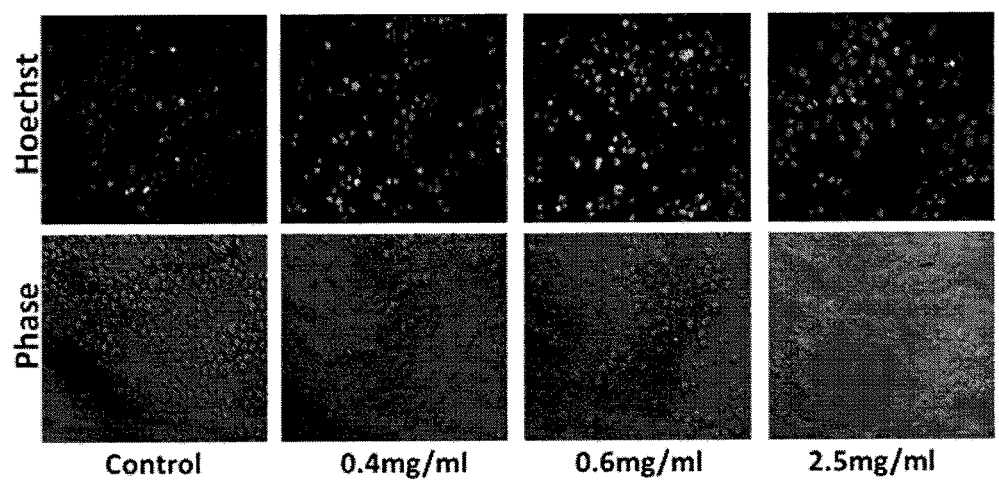
FIG. 17 is a series of 400×-magnified microscope images of DnFADD cells stained with Hoechst 33342 dye (upper row) or viewed under phase contrast illumination (bottom row) after treatment with DRE at concentrations of 0.4 mg/mL, 0.6 mg/mL, and 2.5 mg/mL for 96 hours, and including controls.
Figure 18:
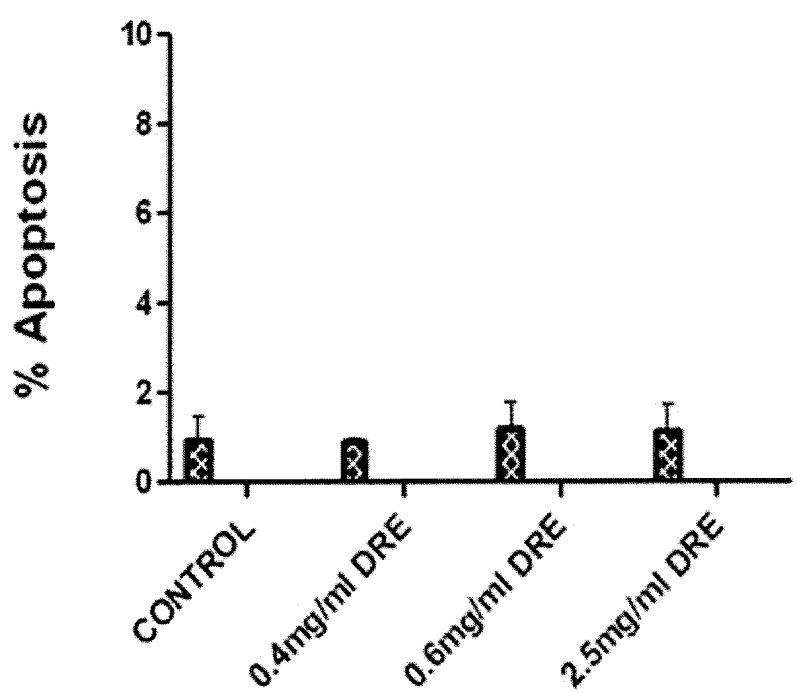
FIG. 18 is a bar graph showing average percent apoptosis of peripheral blood mononuclear cells (y-axis) treated with DRE at concentrations of 0.4 mg/mL, 0.6 mg/mL, and 2.5 mg/mL (x-axis), and including controls.
Figure 19:
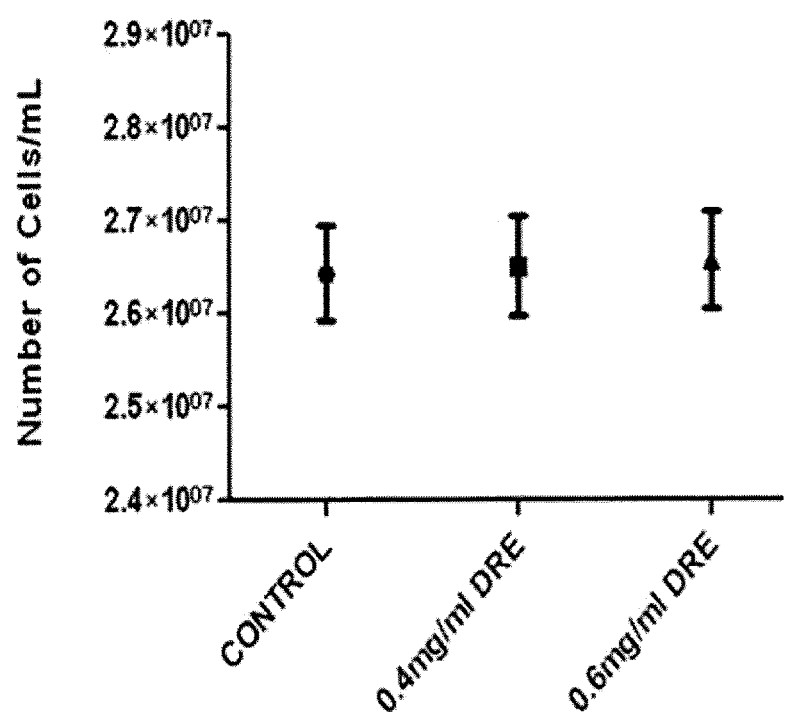
FIG. 19 is a graph showing the concentrations of peripheral blood mononuclear cells (y-axis) treated with DRE at concentrations of 0.4 mg/mL and 0.6 mg/mL (x-axis), and including controls.
Figure 20:
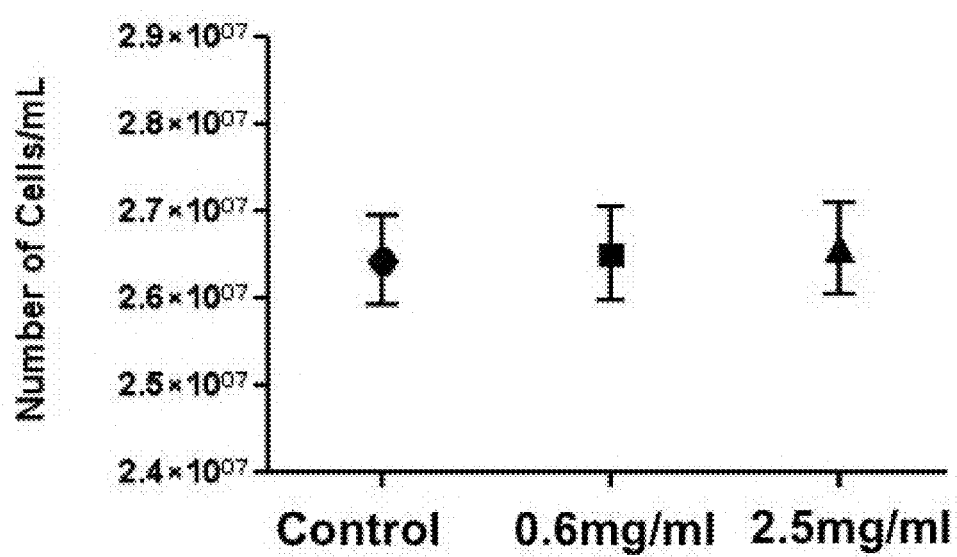
FIG. 20 is a graph showing the concentrations of DnFADD cells (y-axis) treated with DRE at concentrations of 0.6 mg/mL and 2.5 mg/mL (x-axis) as obtained using the trypan blue exclusion assay, and including controls.
Figure 21:
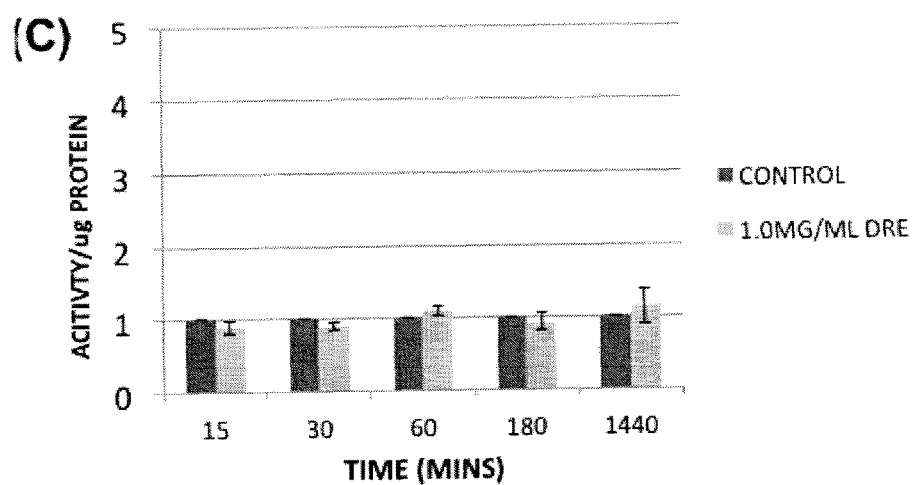
FIG. 21 is a bar graph showing average showing activation or activity of caspase-8 in DnFADD cells (y-axis) treated with DRE for 15 minutes, 30 minutes, 60 minutes, 180 minutes and 1440 minutes, and including controls.

As shown in FIGS. 17 and 20, jurkat cells expressing a dominant-negative FADD (DnFADD) protein, a major component of the death-inducing signaling complex (DISC), were insensitive to apoptosis induced by DRE, further indicating involvement of the extrinsic pathway of cell death. FIG. 21 shows the activation of caspase-8 in DnFADD cells using caspase-8 specific substrate and fluorescence readings, after treatment with DRE at various time points, and which was prepared.

It was furthermore shown that induction of apoptosis in chronic myelomonocytic leukemia cells was hindered after pre-treatment with a pan-caspase inhibitor, z-VAD-fmk.

Non-cancerous peripheral blood mononuclear cells (ncPBMCs), treated with dandelion root extract in parallel, were not susceptible to apoptosis, demonstrating the selectivity of dandelion root extract in cell culture.

Figure 13:
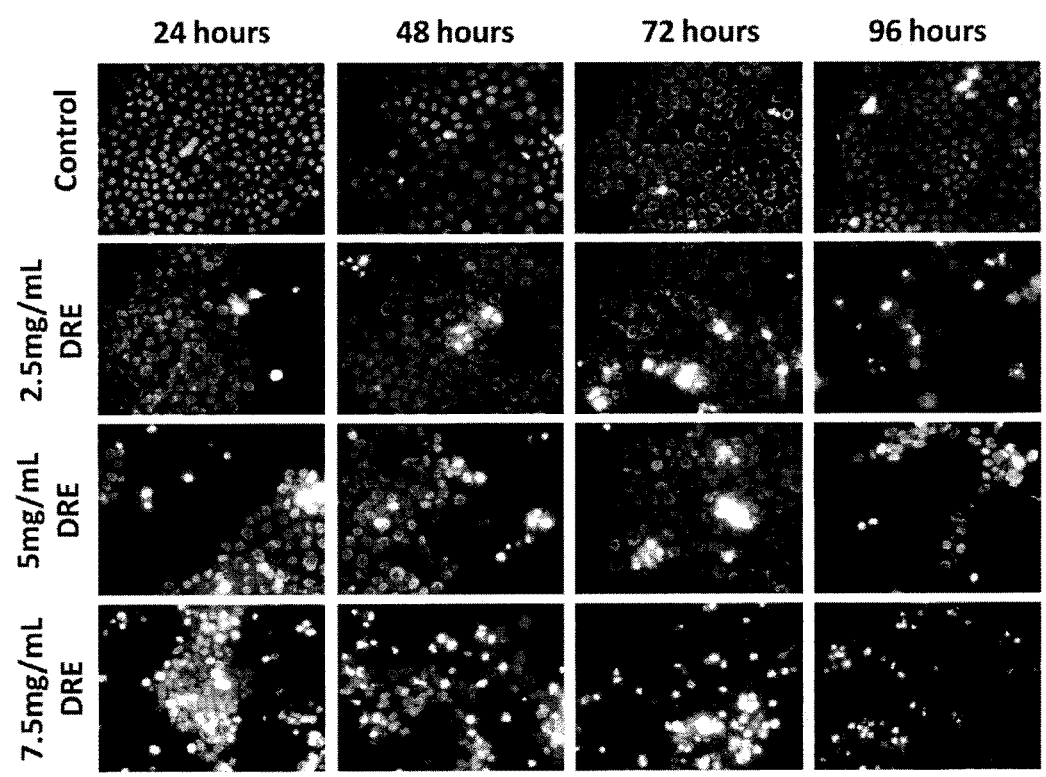
FIG. 13 is series of images of PANC-1 cells stained with Hoechst dye treated with DRE at concentrations of 2.5 mg/mL, 5 mg/mL and 7.5 mg/mL of DRE (rows) for 24 hours, 48 hours, 72 hours and 96 hours (columns), and including controls.
Figure 14:
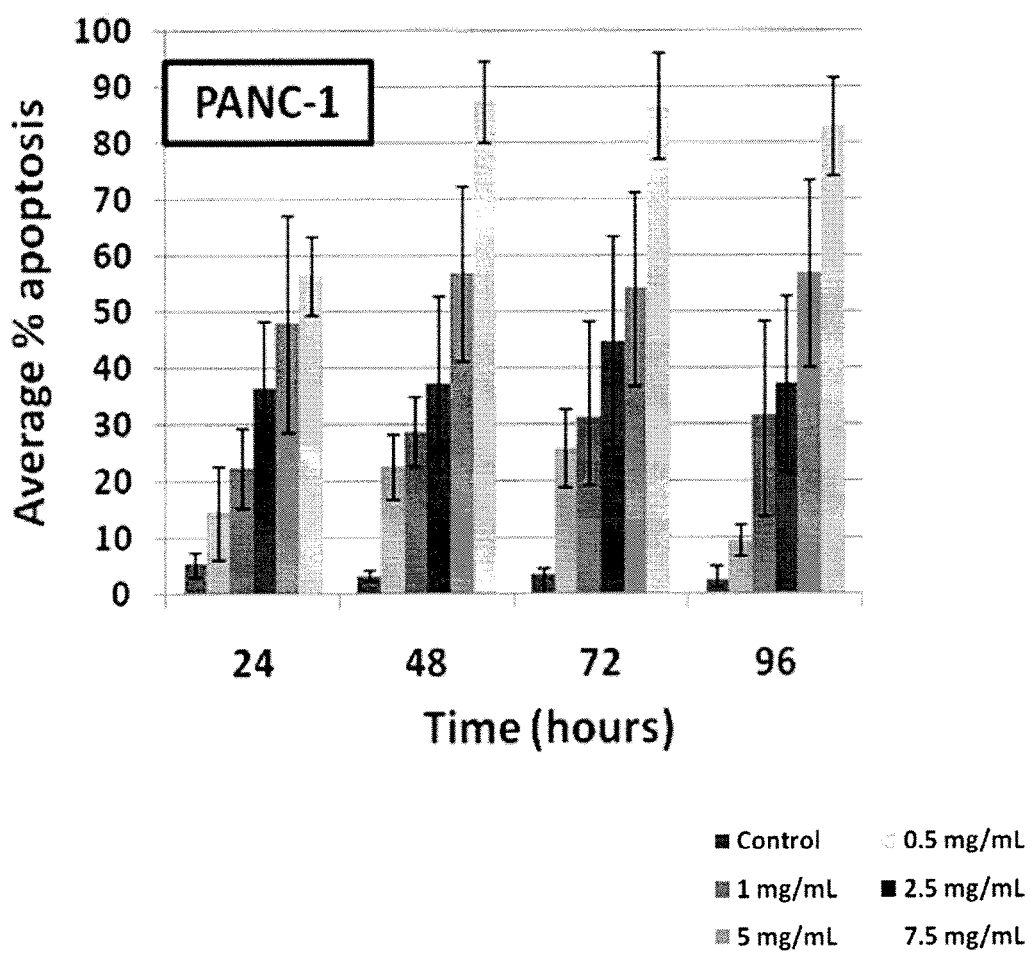
FIG. 14 is a bar graph showing average percent apoptosis of PANC-1 cells (y-axis) treated with DRE at concentrations of 0.5 mg/mL, 1 mg/mL, 2.5 mg/mL, 5 mg/mL and 7.5 mg/mL for 24 hours, 48 hours, 72 hours and 96 hours (x-axis), and including controls.

Results from this study indicate that the dandelion root extract of the present invention is useful as a novel non-toxic alternative to conventional cancer therapy available today. In addition, it is also useful in combination with conventional therapies (with lower concentrations of toxic compounds) to enhance their effects in the treatment of cancer.

iv) Anticancer Activity of Dandelion Root Extract on Aggressive Human Pancreatic Cancer Cells:

The dandelion root extract of the current invention may induce apoptosis in a dose and time dependent manner in aggressive human pancreatic cell lines (BxPC-3 and PANC-1). As shown in FIGS. 13 and 14, increases in brightly stained, condensed nuclei indicative of apoptosis was observed with increasing doses and duration following treatment with DRE. Manual quantification of Hoechst pictures of the PANC-1 cells showed increases in average percent apoptosis in a dose and time dependent manner.

In parallel, similar experiments in non-cancerous Normal Human and Fetal Fibroblasts showed that DRE selectively targets human pancreatic cancer cells, confirming results from previous studies. Early activation of caspase-8 and subsequent activation of caspase-3 indicated that apoptosis induction by DRE is due to activation of the extrinsic pathway of apoptosis.

Figure 24:
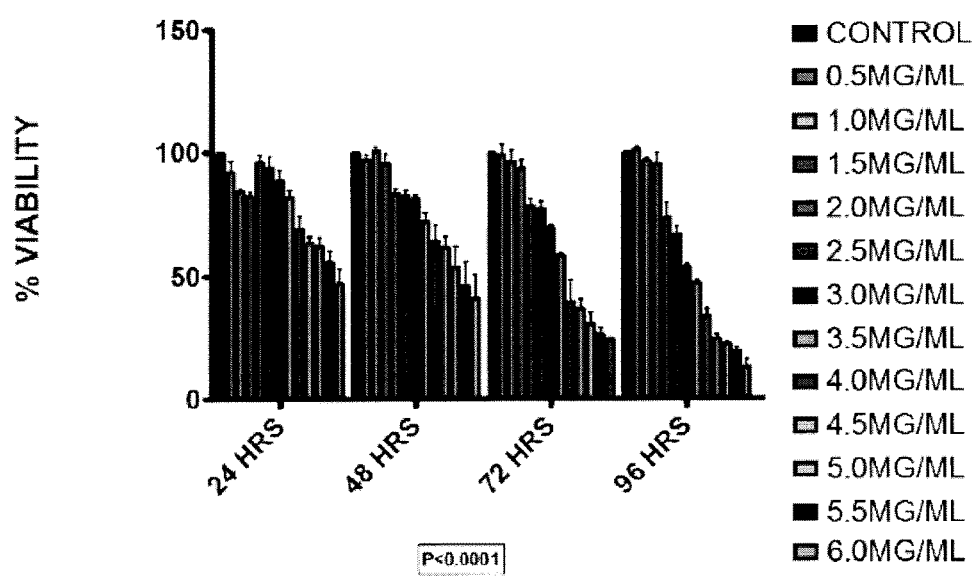
FIG. 24 is a bar graph showing viability percentage of HT-29 human colon cancer cells (y-axis) treated with DRE at concentrations of 0.5 mg/mL, 1.0 mg/mL, 1.5 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL and 6.0 mg/mL for 24, 48, 72 and 96 hours, and including controls.

DRE induced a pro-death form of autophagy in human pancreatic cancer cells. This induction of autophagy corresponds with the destabilization of the mitochondrial membrane potential, which was observed after treatment with DRE. Through revival experiments, it was shown that the signal to commit suicide was retained once the cells had been exposed to DRE.

v) Anticancer Activity of Dandelion Root Extract (DRE) on other Aggressive Human Cancer Cells The DRE of the present invention was shown to be effective in aggressive human colon cancer and neuroblastoma cells. As sown in FIG. 24, the viability of HT-29 human colon cells was affected by treatment with DRE in a time and dose dependent manners. $EC_{50}$ was determined to be 3.0 mg/mL at 96 hours. FIG. 24 was prepared from data gathered in a WST-1 cell proliferation assay. In particular, HT-29 human colon cancer cells were seeded on 96-well plates (about 5000 cells/well), and then treated with DRE at different concentrations for 24, 48, 72 and 96 hours.

vi) Evaluation of Toxicity of Dandelion Root Extract in Mouse Models

Figure 15:
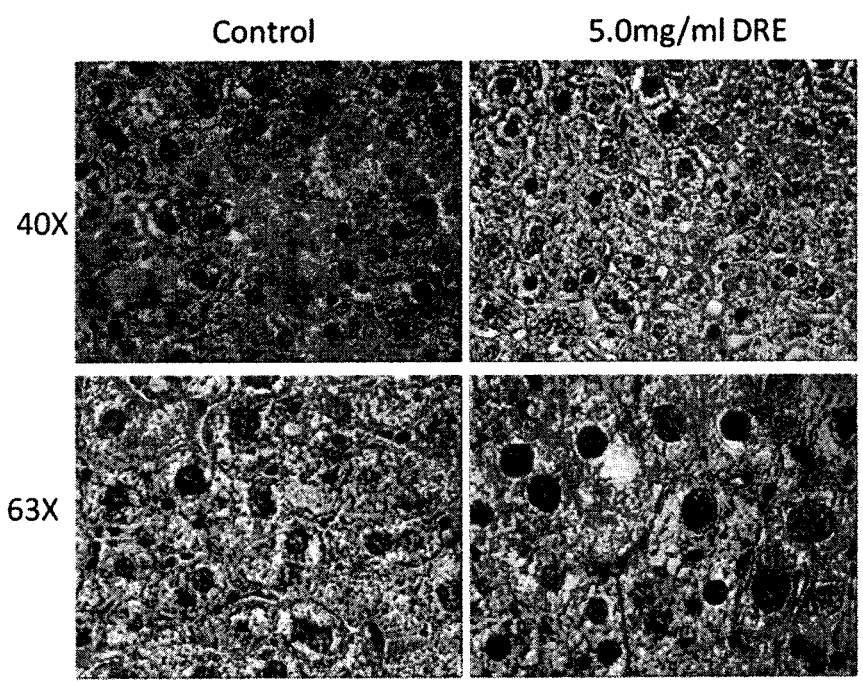
FIG. 15 is series of images of hematoxylin and eosin stained liver tissue of balb/c mice at 40× or 63× magnification (top and bottom rows, respectively) after treatment with plain filter water or water containing 5.0 mg/mL of DRE for a month (left and right columns, respectively).
Figure 16:
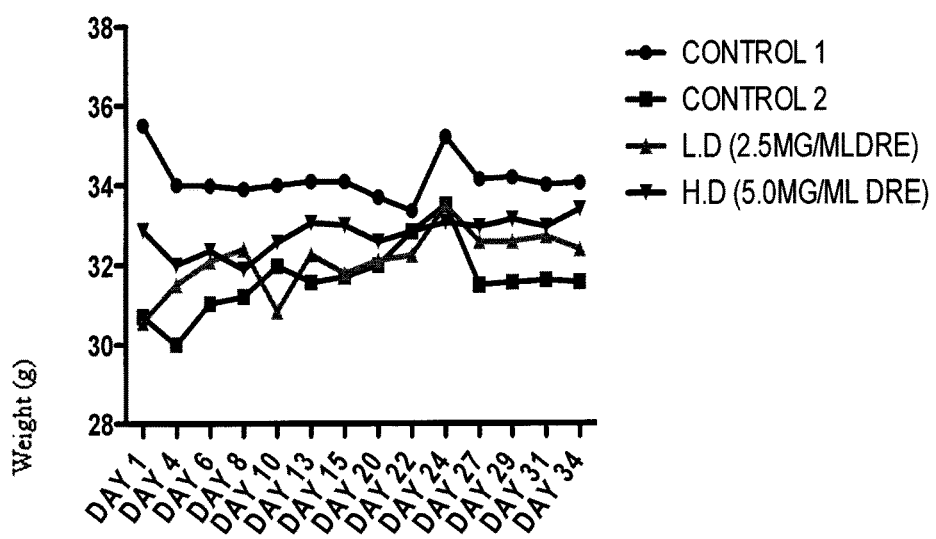
FIG. 16 is a line graph showing weights of balb/c mice (y-axis) treated with DRE at concentrations of 2.5 mg/mL or 5.0 mg/mL on different days (x-axis), and including controls.
Figure 25:
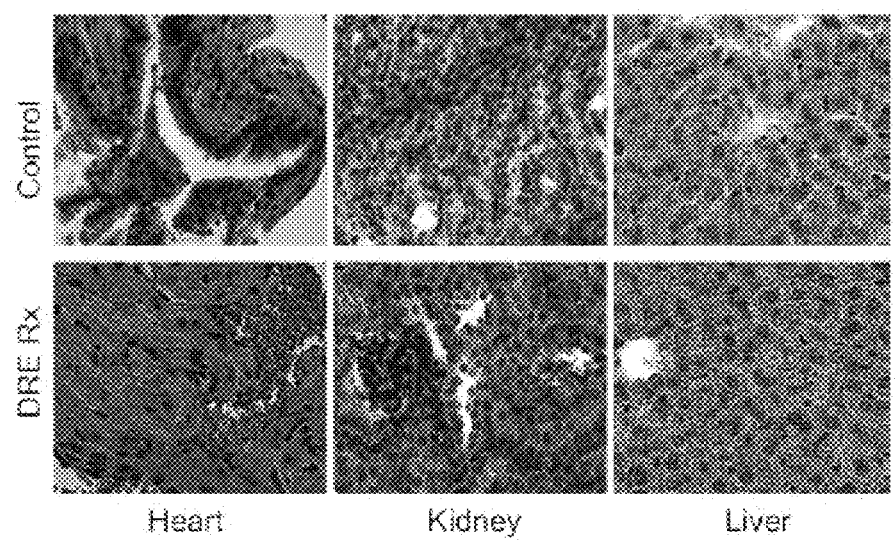
FIG. 25 is series of images of hematoxylin and Eosin stained heart, kidney and liver tissues of balb/c mice after treatment with plaint filtered water (upper rows) or with DRE for a month (bottom rows).
Figure 26:
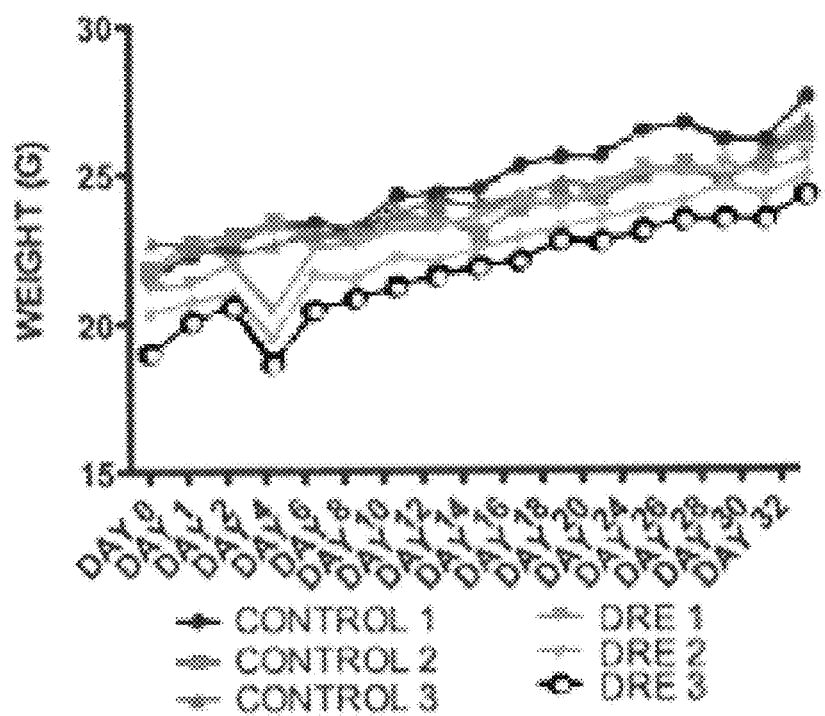
FIG. 26 is a line graph showing weights of balb/c mice (y-axis) treated with DRE on different days (x-axis), and including controls.

The toxicity of the extract of the present invention in in vivo mouse models in the absence of any cancers using male balb/c mice was studied. There was a control group on plain filtered water regimen, and two DRE groups; a low dose group, given 2.5 mg/ml DRE (equivalent human dose of 105 g/day for a 70 kg patient) in their drinking water and a high dose group, given 5.0 mg/ml DRE in their drinking water. On an average, each mouse consumed approximately 5 mL of drinking solution per day, which translated to 500 mg/kg/day (low dose group, extracted from 5 g of dried root with an extraction ratio of 1:10) and 1,000 mg/kg/day (high dose group, extracted from 10 g of dried root with the same extraction ratio of 1:10). Such doses were higher than what was necessary for apoptotic induction in the in vitro studies. These mice were given DRE in their water every day and monitored over one month, with the weights being measured every other day as shown in FIGS. 16 and 26 of two separate experiments. Following 34 days, the mice were sacrificed according to the Animal Care Committee guidelines of the University of Windsor and the organs (liver, kidneys and heart) were removed for pathological analysis. As further shown in FIGS. 15 and 25, no toxicity on these mice were seen on the basis of measured weight and pathology. There was no difference between the control untreated mice and the DRE-fed mice in terms of weight change and pathology of the organs obtained.

Figure 27:
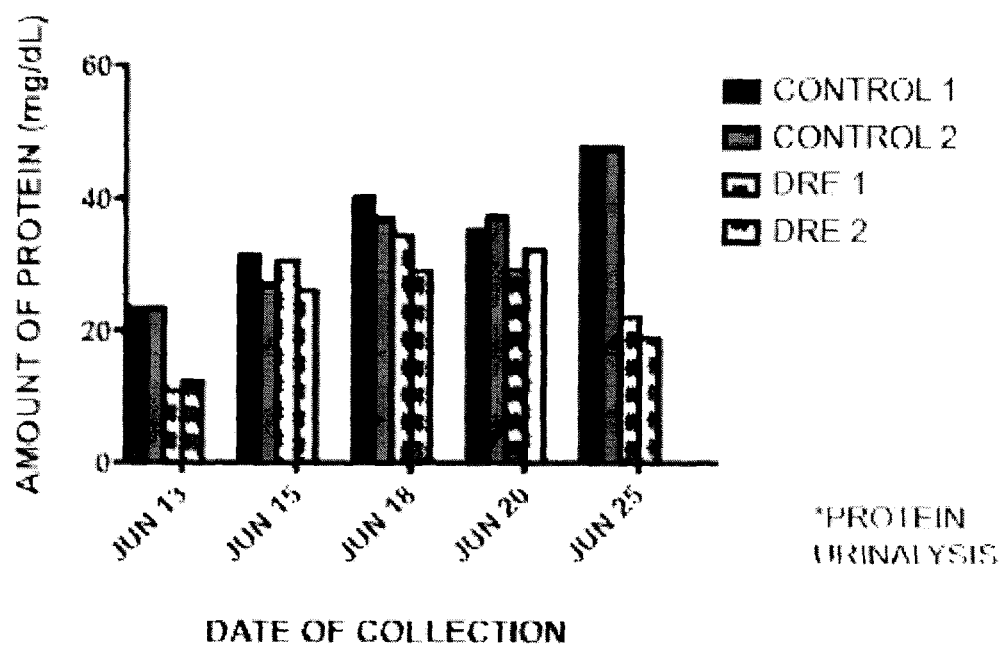
FIG. 27 is a bar graph showing the amount of protein (y-axis) detected in urine samples collected from balb/c mice treated with DRE, and including controls.

Further efficacy studies were performed with four mice in the DRE treated group that were given 500 mg/kg/day of DRE for a total of 35 days. Their tissues from liver, kidneys and heart were analyzed for any toxic indication. The tissues did not show any change, compared to the water-fed control mice. For further toxic indications, urine was also obtained from each group of mice and analyzed for protein content, using a Bradford protein estimation assay. As shown in FIG. 27, lower levels of protein were found in the DRE-fed mice, compared those of the control mice. These results indicate that DRE of the present invention is non-toxic and well-tolerated in mice, as a supplement to their drinking water, over a long period of time.

Further toxicity tests performed in vivo with mouse models confirmed that the extract of the present invention does not present any significant toxicity at daily doses as high as 3% body weight, 1.0 g/kg/day or 100 g/day.

Figure 22:
FIG. 22 is a series of images of peripheral blood mononuclear cells isolated from a newly-diagnosed leukemia patient, and stained with Hoescht or Annexin-V stain (top and bottom rows, respectively) after treatment with DRE at concentrations of 1.0 mg/mL, 2.5 mg/mL and 5.0 mg/mL, and including controls.
Figure 23:
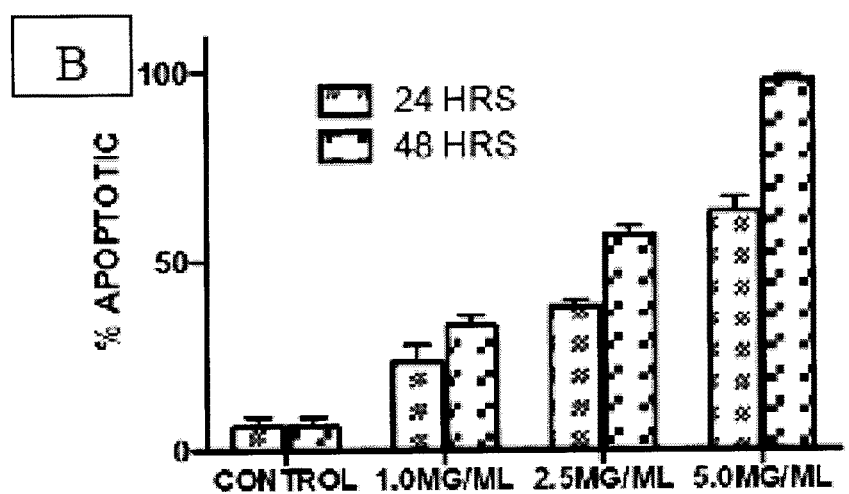
FIG. 23 is a bar graph showing the percentage of peripheral blood mononuclear cells isolated from a newly-diagnosed leukemia patient, and induced to apoptosis (y-axis) after 24-hour or 48-hour treatment with DRE at concentrations of 1.0 mg/mL, 2.5 mg/mL and 5.0 mg/mL, and including controls.

Based on the toxicity tests, the effective dosage for human patients may preferably be about 0.5 to 4.0 g/day/patient (with 70 kg weight), or more preferably 2.0 g/day/patient (which is less than 2% of well-tolerated dose in mice). One human patient who was treated with the DRE of the present invention was tolerant and responsive to 23 mg/kg/day.

vii) Anticancer Activity of Dandelion Root Extract in Patient-derived ex-vivo Samples of Leukemia The effect of DRE in patient-derived leukemia samples from newly diagnosed patients were studied. The experiment was performed using samples from 9 patients. Blood samples were obtained from newly diagnosed patients and peripheral blood mononuclear cells (PBMCs) were isolated and treated with the DRE of the current invention. As shown FIGS. 22 and 23, the DRE of the present invention effectively induced apoptosis in PBMCs obtained from leukemia patients in a dose and time dependent manner. FIG. 23 was obtained by manual quantification of Hoechst pictures from six different patients.

viii) Efficacy of Dandelion Root Extract Against Human Colon Cancer Xenotransplant in Immunocompromised Mice To evaluate the efficacy of DRE of the present invention in in vivo models of various cancers, xenotransplants of colon cancer models were made using immunocompromised CD-1 nu/nu mice. In particular, HT-29 cells were injected on either side of the mice underneath the skin, and allowed to form tumors for a week prior to commencing treatments. The mice were divided into two groups (four mice per group), one on plain filtered water regimen and the other was given 2.5 mg/mL aqueous DRE (400 mg/kg/day extracted from 5 g of dried root with an extraction ratio of 1:10) in their drinking water for a month. The weight of each mouse was obtained every other day and following a month of treatment, the mice were sacrificed and the organs were obtained for pathological analysis.

Figure 28:
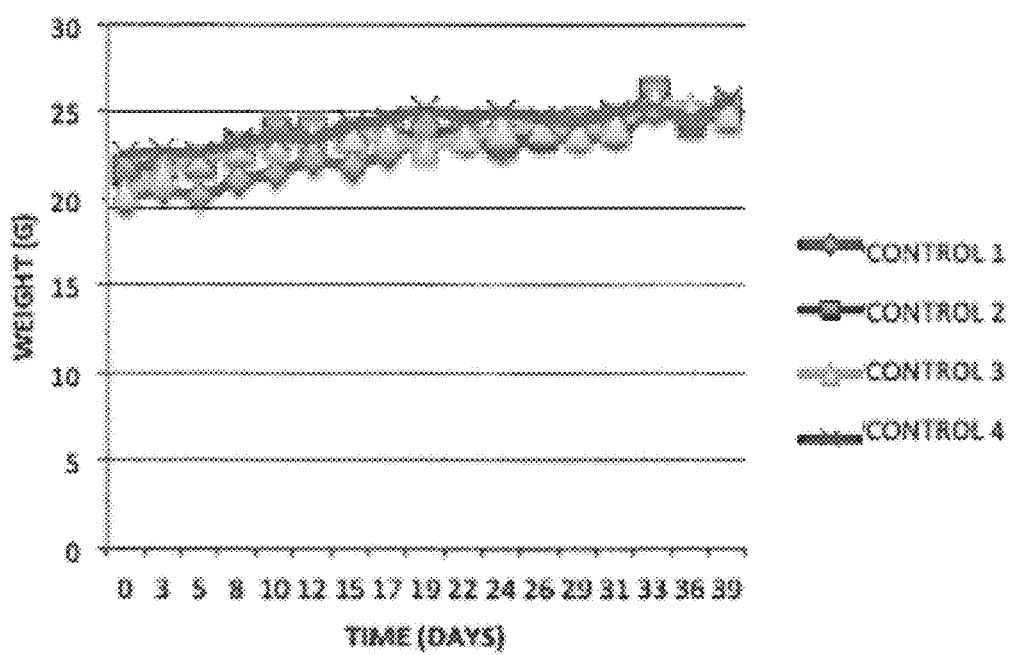
FIG. 28 is a line graph showing weights of control CD-1 nu/nu mice (y-axis) on different days (x-axis).
Figure 29:
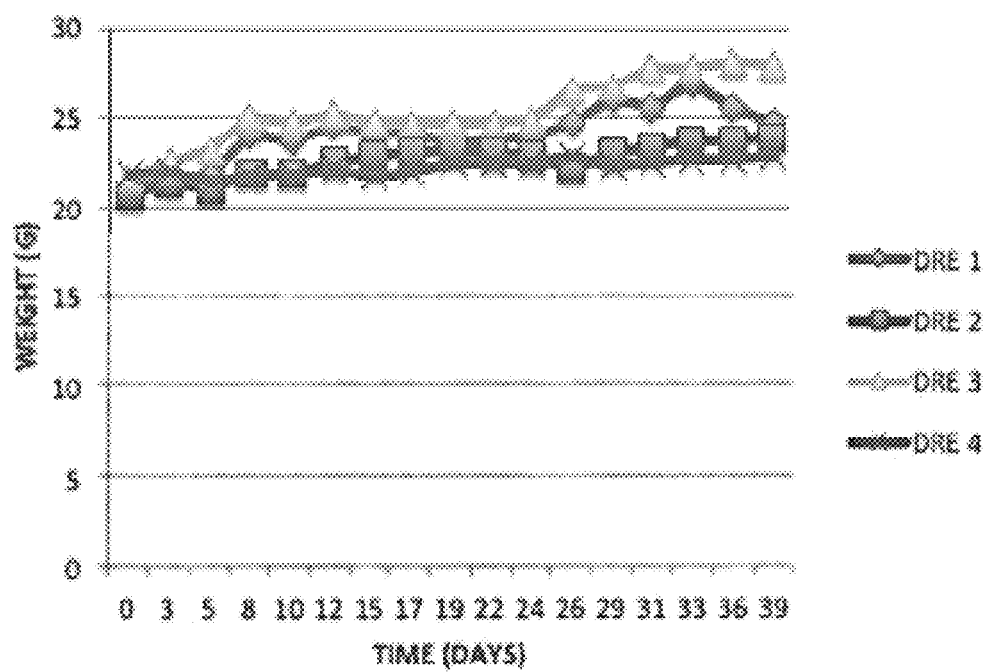
FIG. 29 is line graph showings weights of CD-1 nu/nu mice (y-axis) treated with DRE at the concentration of 2.5 mg/mL on different days (x-axis).
Figure 30:
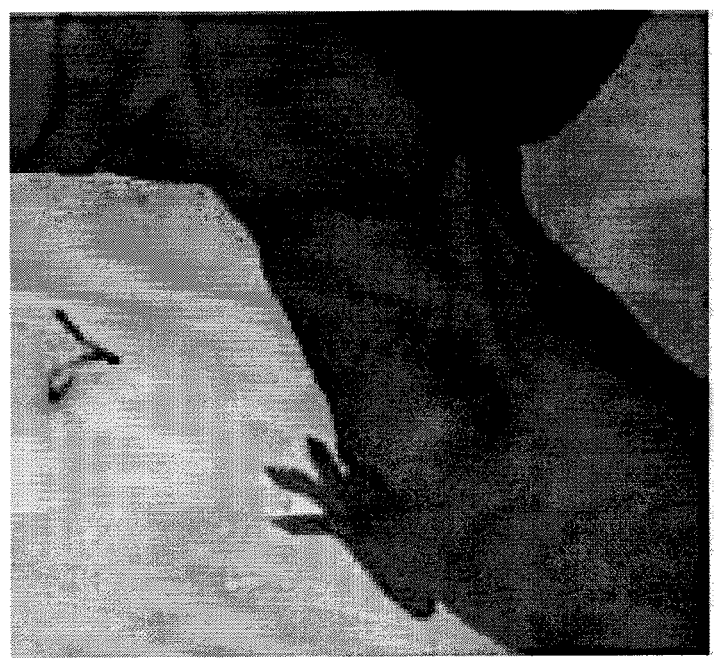
FIG. 30 is a photograph of a CD-1 nu/nu mouse transplanted with HT-29 cells, and treated with filtered plain filtered water for three weeks.
Figure 31:
FIG. 31 is a photograph of CD-1 nu/nu mouse transplanted with HT-29 cells, and treated with DRE at the concentration of 2.5 mg/mL for three weeks.
Figure 32:
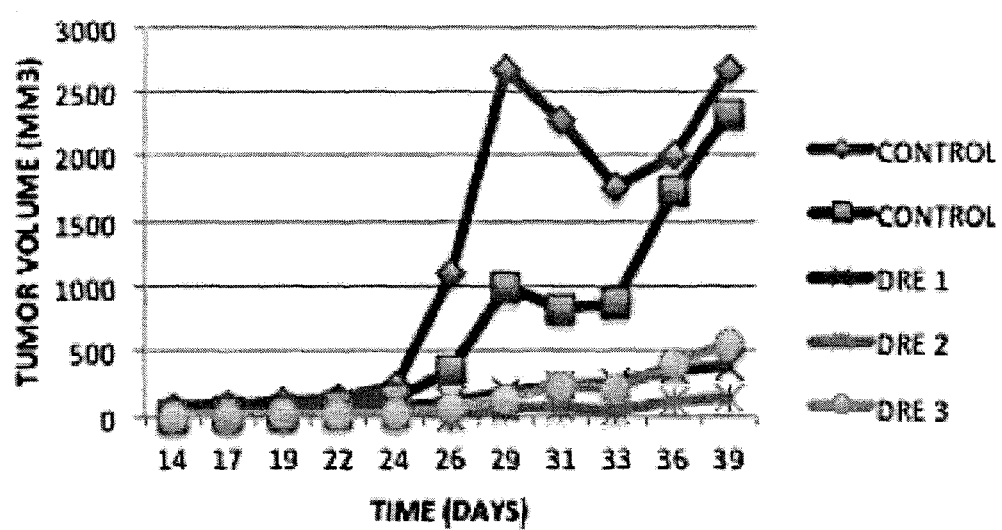
FIG. 32 is a bar graph showing tumor volumes (y-axis) of CD-1 nu/nu mice treated with DRE at the concentration of 2.5 mg/mL on different days (x-axis), and including controls.

As shown in FIGS. 28 and 29, no differences in weights between the control, water-fed mice and the DRE fed mice, confirming lack of toxicity. FIGS. 30 and 31, respectively, are photographs of the CD-1 nu/nu mice after three weeks of treatment with plain filtered water or DRE. As shown in FIG. 32, water-fed mice had larger tumor volumes compared to the DRE-fed mice, indicating the efficacy of DRE against colon cancer in in vivo models.

Figure 33:
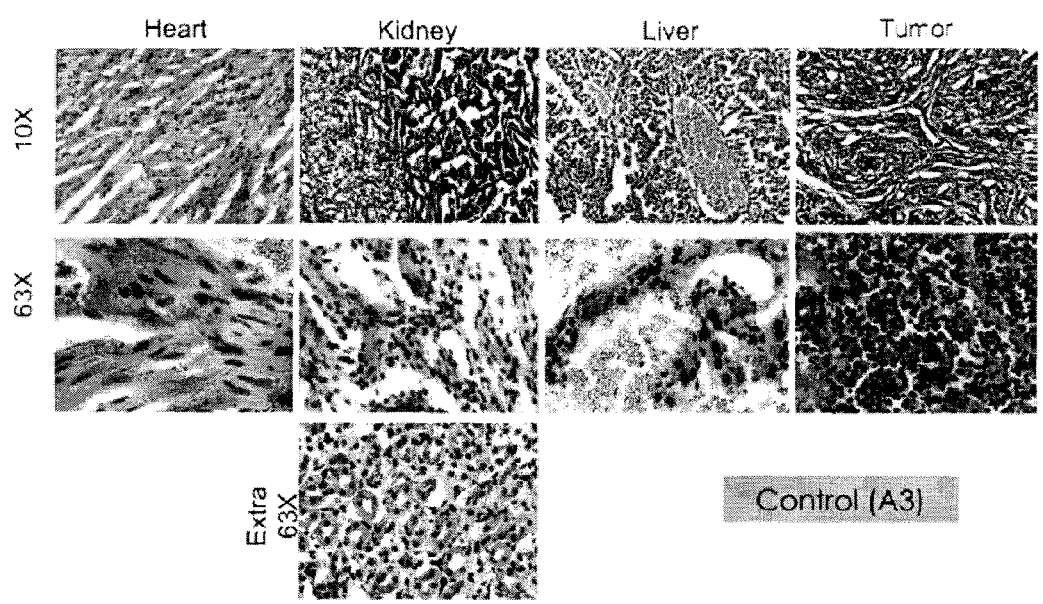
FIG. 33 is series of images of hematoxylin and eosin stained heart, kidney, liver and xenotransplanted tumor tissues of CD-1 nu/nu mice at 10× or 63× magnification (top and bottom two rows, respectively) after treatment with plain filtered water for a month.
Figure 34:
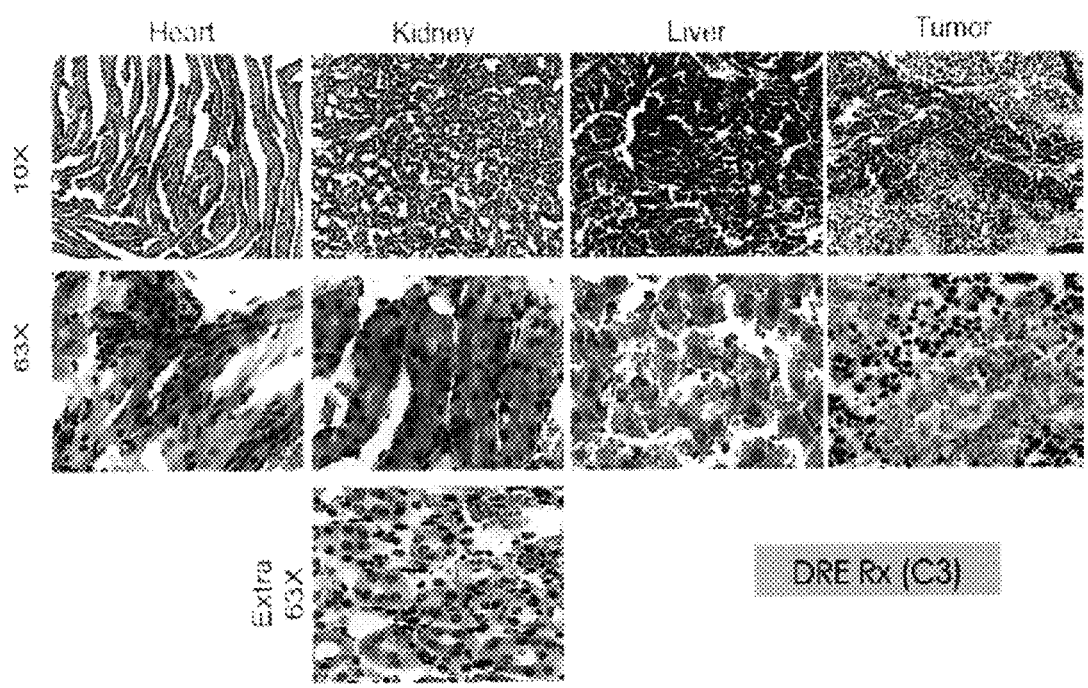
FIG. 34 is series of images of hematoxylin and eosin stained heart, kidney, liver and xenotransplanted tumor tissues of CD-1 nu/nu mice at 10× or 63× magnification (top and bottom two rows, respectively) after treatment with DRE at the concentration of 2.5 mg/mL for a month.

As further shown in FIGS. 33 and 34, tissue histochemical state of heart kidney and liver do not show any difference between control and DRE-treated animals indicating no toxicity to these tissues. On the other hand, there is clear difference in the tumor histochemistry of control and treated animals where significant decrease in the number of tumor cell nuclei could be seen.

Similar studies were done using HCT116 cells instead of HT-29 cells, and showed similar efficacy and toxicity results.

The above results indicate that DRE was able to halt the growth of colon tumors in the DRE treatment group, compared to the water-fed groups. There was no toxicity observed in the DRE treated groups, confirming the toxicity evaluation results. These results suggest the potential efficacy of DRE in in vivo models of colon cancer.

ix) Clinical Data

A 70 year old man with refractory M5 acute myeloid leukemia reported to have achieved a sustained remission lasting over 18 months with DRE alone. Although he obtained complete remission from his acute monocytic leukemia, he continued to have evidence of chronic mylelomonocytic leukemia (CMML). His peripheral monocyte count was seen to rise when he decreased his frequency of DRE consumption and similarly was controlled when he increased the amount of DRE consumed. Temporary responses in two women with chronic myelomonocytic leukemia, using DRE alone was also observed.

Transient responses in patients consuming this product were reported. One patient with refractory acute myeloid leukemia started DRE and hydroxyurea at the same time, with immediate and dramatic response to this combination. The patient had multiple large skin nodules that went into remission within 24 hours. The patient maintained this response for one month, despite stopping the hydroxyurea after only 24 hours. He tolerated the drug extremely well, with no reported toxicity.

Another patient took the DRE for refractory Hodgkin's lymphoma. The patient was a 40 year female who failed multiple chemotherapies and autologous stem cell transplant. The patient undertook concomitant chemotherapy in the form of cyclophosphamide and etoposide. She suffered from cytopenias from this combination, but was suffering cytopenia from these medications before the DRE was added. She had a dramatic, but temporary response on CT scan when the DRE was added. She progressed after three months on the product, and developed pancreatitis following this progression.

Many patients having used DRE for various malignancies including colorectal cancer reported excellent tolerance, and self-reported responses. Another patient with Hodgkin's lymphoma reported an apparent remarkable response to the treatment with DRE.

Other anticancer ingredients or drugs, which do not impair the functions of the root extract may be added to the medicament of the present invention. Such anticancer ingredients may include, but not limited to, an antifolate, a 5-fluoropyrimidine (including 5-fluorouracil), a cytidine analogue such as β-L-1,3-dioxolanyl cytidine or β-L-1,3-dioxolanyl 5-fluorocytidine, antimetabolites (including purine antimetabolites, cytarabine, fudarabine, floxuridine, 6-mercaptopurine, methotrexate, and 6-thioguanine), hydroxyurea, mitotic inhibitors (including CPT-11, Etoposide (VP-21), taxol, and vinca alkaloids such as vincristine and vinblastine), an alkylating agent (including but not limited to busulfan, chlorambucil, cyclophosphamide, ifofamide, mechlorethamine, melphalan, and thiotepa), nonclassical akylating agents, platinum containing compounds, bleomycin, an anti-tumor antibiotic, an anthracycline such as doxorubicin and dannomycin, an anthracenedione, topoisomerase II inhibitors, hormonal agents (including but not limited to corticosteriods (dexamethasone, prednisone, and methylprednisone), androgens such as fluoxymesterone and methyltestosterone), estrogens such as diethylstilbesterol, antiestrogens such as tamoxifen, LHRH analogues such as leuprolide, antiandrogens such as flutamdie, aminogluetethimide, megestrol acetate, and medroxyprogesterone, asparaginase, carmustine, lomustine, hexamethyl-melamine, dacarbazine, mitotane, streptozocin, cisplatin, carboplatin, levamasole, and leucovorin. Preferably, the anticancer agent is metformin, hydroxyurea, cyclophosphamide or etoposide. The compounds of the present invention can also be used in combination with enzyme therapy agents and immune system modulators such as an interferon, interleukin, tumor necrosis factor, macrophage colony-stimulating factor and colony stimulating factor. The root extract may be administered to a patient by any appropriate route which, for example, may include oral, parenteral, intravenous, intradermal, transdermal, mucosal, subcutaneous, and topical.

Preferably, the root extract is administered orally. A number of administration/dosage experiments showed that the medicament of the present invention may produce greater anticancer activity if ingested orally, and possibly exposed to the subject's digestive system. The root extract may be orally administered in powder or liquid extract form without further modifications. Alternatively, the root extract may be solubilized in a liquid, most preferably in water, the liquid containing the extract is orally administered. To prevent inadvertent introduction of a bacteria or bacterial infection, the extract of the present invention may be boiled into a tea and the tea containing the extract may be orally administered. The root extract may alternatively be enclosed in capsules or compressed into tablets. Such capsules or tablets may be purified to remove impurities and/or bacteria, or further include an inert diluent, an edible carrier, binding agents, and/or adjuvant materials.

The tablets, capsules, and the like can contain any of the following ingredients, or compounds of similar nature: a binder such as microcrystalline cellulose, gum tragacanth or gelatin; an excipient such as starch or lactose; a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to the aforementioned materials, a liquid carrier such as fatty oil. In addition, dosage unit forms can contain various other materials which modify the physical form of the dosage unit, for example, coating of sugar, shellac, or other enteric agents.

It is to be noted that dosage will vary with the conditions, age, body weight and severity of the cancer to be treated. It will be readily apparent to a person skilled in the art that for each patient, specific dosage regimens could be adjusted over time according to individual needs. The root extract may be administered once or may be divided into a number of smaller doses to be administered at varying intervals of time.

The medicament of the present invention is suitable for treatment and/or prevention of a cancer, including that of skin tissues, organs, bone, cartilage, blood and vessels. The root extract may be used to treat variety of cancers including, but not limited to, cancer of the head, neck, eye, mouth, throat, esophagus, chest, bone, lung, colon, rectum, stomach, prostate, breast, ovaries, kidney, liver, pancreas and brain. The cancer encompasses primary and metastatic cancers.

The most preferred embodiments of the present invention are described hereto. The most preferred embodiments are provided as mere examples which are in no way intended to limit the scope of the present invention. It will be readily apparent to a person skilled in the art that variations and modifications may be made to the most preferred embodiments within the scope of the present invention.

We claim:

1. A method for preparing a medicament for the treatment of a cancer, the method comprising the steps of:
   (a) selecting a dormant *Taraxacum* plant root obtained prior to plant blooming or budding or after cessation of bud growth;
   (b) freezing the *Taraxacum* plant root to obtain a frozen plant root stock, said freezing step being selected to effect at least partial disruption of one or more root cells;
   (c) dry grinding the frozen plant root stock to obtain a ground plant root powder, wherein during said dry grinding step the frozen root stock is maintained at a grinding temperature below about 40° C.;
   (d) soaking or steeping the ground plant root powder with a solvent comprising one or more of water, methanol, ethanol, n-propanol, isopropanol and n-butanol to obtain a mixture having a liquid extract portion and a solid particle portion;
   (e) separating the liquid extract portion from the solid particle portion to provide a separated liquid extract;
   (f) optionally freeze drying the separated liquid extract to obtain an extract powder; and
   (g) optionally mixing an effective amount of the extract powder with one or more of a pharmaceutically acceptable carrier, a diluent, a binding agent, an adjuvant, and an anticancer agent, to produce said medicament.

2. The method of claim 1, wherein said cancer is a colon cancer, a pancreatic cancer, a blood cancer or a skin cancer.

3. The method of claim 2, wherein said cancer comprises said blood cancer or said skin cancer, and is selected from the group consisting of chronic lymphoid leukemia, chronic myeloid leukemia, chronic monocytic myeloid leukemia, Hodgkin's lymphoma, and melanoma.

4. The method of claim 1, wherein prior to said freezing step, the method further comprises drying said plant root to a relative humidity between about 5% to about 10%.

5. The method of claim 1, wherein said dormant *Taraxacum* plant root is harvested within about 90 days prior to a blooming or budding season of the *Taraxacum* plant.

6. The method of claim 1, wherein said *Taraxacum* plant root is from a plant belong to a species selected from the group consisting of *T. officinale, T. erythrospermum, T. albidum, T. japonicum, T. laevigatum, T. erythrospermum* and *T. californicum*.

7. The method of claim 1, wherein said freezing step comprises contacting or submerging the plant root in liquid nitrogen, or freezing the plant root to an average freezing temperature between about −210° C. and about −30° C.

8. The method of claim 1, wherein said dry grinding step comprises dry grinding the frozen plant root stock to an average particle size of less than about 100 μm.

9. The method of claim 1, wherein said dry grinding step comprises dry grinding the frozen plant root stock with a grinder selected from the group consisting of a pulverizer, an impingement grinder and a micronized milling machine, and wherein the grinder or a component thereof is cooled below about −25° C. to prevent heating on contact with the frozen plant root stock or the ground plant root powder.

10. The method of claim 9, wherein the grinder or a component thereof is cooled with liquid nitrogen.

11. The method of claim 1, wherein said solvent comprises one or more of water, pentane, cyclopentane, cyclohexane, benzene, toluene, 1,4-dioxane, chloroform, diethyl ether, dichloromethane, tetrahydrofuran, ethyl acetate, acetone, dimethylformamide, acetonitrile, dimethyl sulfoxide, propylene carbonate, formic acid, n-butanol, isopropanol, n-propanol, ethanol, methanol, and acetic acid.

12. The method of claim 1, wherein said solvent is water, ethanol or a mixture of water and ethanol.

13. The method of claim 1, wherein said soaking or steeping step comprises soaking the ground plant root powder in water at a soaking temperature between about 5° C. and about 100° C. for a period of about 5 minutes to about 24 hours with or without stirring.

14. The method of claim 1, wherein said separation step comprises at least one of filtration and centrifugation, and wherein the filtration is performed once or more than once using a plurality of filters of same or different pore sizes, and the centrifugation is performed at 5000× g to 8000× g.

15. The method of claim 1, wherein said separation step comprises filtering the mixture at least twice with a first filter having a first pore size of about 0.45 μm and a second filter having a second pore size of about 0.22 μm, and wherein one or both said filters are selected to remove a bacteria.

16. The method of claim 1, wherein prior to the dry grinding step, the method further comprises dicing said plant root to produce a plurality of root pieces having an average dimension selected between about 0.2 cm and about 1.5 cm.

17. The method of claim 1, wherein said grinding temperature is below about −25° C., or below about −40° C.

18. The method of claim 1, wherein said anticancer agent is one or more of metformin, hydroxyurea, cyclophosphamide and etoposide.

19. The method of claim 1, wherein said medicament comprises a dosage form containing the extract powder in a range of about 5 mg/kg weight/day to about 1000 mg/kg weight/day.

20. The method of claim 1, wherein said medicament comprises a daily dosage form containing the extract powder in a range of about 0.5 g to about 70 g.

21. The method of claim 5, wherein said dormant *Taraxacum* plant root is harvested about 30 days prior to said blooming or budding season.

* * * * *